(12) United States Patent
Thomas et al.

(10) Patent No.: US 12,114,866 B2
(45) Date of Patent: Oct. 15, 2024

(54) INTEROPERATIVE CLIP LOADING DEVICE

(71) Applicant: Covidien LP, Mansfield, MA (US)

(72) Inventors: Justin Thomas, New Haven, CT (US);
Jacob C. Baril, Norwalk, CT (US);
Matthew A. Dinino, Newington, CT
(US); Roy J. Pilletere, Middletown, CT
(US)

(73) Assignee: Covidien LP, Mansfield, MA (US)

( * ) Notice: Subject to any disclaimer, the term of this patent is extended or adjusted under 35 U.S.C. 154(b) by 949 days.

(21) Appl. No.: 17/146,585

(22) Filed: Jan. 12, 2021

(65) Prior Publication Data

US 2021/0298758 A1 Sep. 30, 2021

Related U.S. Application Data

(60) Provisional application No. 63/000,091, filed on Mar. 26, 2020.

(51) Int. Cl.
*A61B 17/128* (2006.01)
*A61B 17/122* (2006.01)
*A61B 17/00* (2006.01)

(52) U.S. Cl.
CPC .......... *A61B 17/128* (2013.01); *A61B 17/122* (2013.01); *A61B 17/1222* (2013.01); *A61B 2017/0042* (2013.01); *A61B 17/1227* (2013.01)

(58) Field of Classification Search
None
See application file for complete search history.

(56) References Cited

U.S. PATENT DOCUMENTS

| 3,040,749 A | 6/1962 | Payton |
| 3,120,230 A | 2/1964 | Skold |
| 3,363,628 A | 1/1968 | Wood |
| 3,439,523 A | 4/1969 | Wood |
| 3,638,847 A | 2/1972 | Noiles et al. |
| 3,675,688 A | 7/1972 | Bryan et al. |
| 3,713,533 A | 1/1973 | Reimels |
| 3,735,762 A | 5/1973 | Bryan et al. |
| 3,867,944 A | 2/1975 | Samuels |
| 4,076,120 A | 2/1978 | Carroll et al. |
| 4,146,130 A | 3/1979 | Samuels et al. |
| 4,187,712 A | 2/1980 | Samuels et al. |

(Continued)

FOREIGN PATENT DOCUMENTS

| AU | 2013254887 A1 | 11/2013 |
| BE | 654195 A | 2/1965 |

(Continued)

OTHER PUBLICATIONS

International Search Report and Written Opinion corresponding to International Application No. PCT/US18/050316 mailed Dec. 31, 2018.

(Continued)

*Primary Examiner* — Tanzim Imam
(74) *Attorney, Agent, or Firm* — Draft Masters IP, LLC

(57) ABSTRACT

An intraoperative clip loading device includes an elongate body that can be positioned at a surgical site through a cannula during an endoscopic surgical procedure to provide a supply of ligation clips to the clip applier. The elongate body includes structure for supporting and advancing the ligation clips within the elongate body.

20 Claims, 14 Drawing Sheets

(56) References Cited

U.S. PATENT DOCUMENTS

| | | |
|---|---|---|
| 4,212,303 A | 7/1980 | Nolan |
| 4,212,390 A | 7/1980 | Raczkowski et al. |
| 4,226,242 A | 10/1980 | Jarvik |
| 4,242,902 A | 1/1981 | Green |
| 4,294,355 A | 10/1981 | Jewusiak et al. |
| 4,296,751 A | 10/1981 | Blake, III et al. |
| 4,344,531 A | 8/1982 | Giersch |
| 4,346,869 A | 8/1982 | MacNeill |
| 4,361,229 A | 11/1982 | Mericle |
| 4,372,316 A | 2/1983 | Blake, III et al. |
| 4,390,019 A | 6/1983 | LeVeen et al. |
| 4,408,603 A | 10/1983 | Blake, III et al. |
| 4,412,539 A | 11/1983 | Jarvik |
| 4,412,617 A | 11/1983 | Cerwin |
| 4,418,694 A | 12/1983 | Beroff et al. |
| 4,449,531 A | 5/1984 | Cerwin et al. |
| 4,471,780 A | 9/1984 | Menges et al. |
| 4,476,865 A | 10/1984 | Failla et al. |
| 4,478,218 A | 10/1984 | Mericle |
| 4,480,640 A | 11/1984 | Becht |
| 4,480,641 A | 11/1984 | Failla et al. |
| 4,485,953 A | 12/1984 | Rothfuss |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,550,729 A | 11/1985 | Cerwin et al. |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 1,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,936,447 A | 6/1990 | Peiffer |
| 4,942,886 A | 7/1990 | Timmons |
| 4,957,500 A | 9/1990 | Liang et al. |
| 4,961,499 A | 10/1990 | Kulp |
| 4,966,603 A | 10/1990 | Focelle et al. |
| 4,967,949 A | 11/1990 | Sandhaus |
| 4,971,198 A | 11/1990 | Mericle |
| 4,972,949 A | 11/1990 | Peiffer |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,046,611 A | 9/1991 | Oh |
| 5,046,624 A | 9/1991 | Murphy et al. |
| 5,047,038 A | 9/1991 | Peters et al. |
| 5,049,152 A | 9/1991 | Simon et al. |
| 5,049,153 A | 9/1991 | Nakao et al. |
| 5,050,272 A | 9/1991 | Robinson et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,416 A | 4/1993 | Taylor |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey et al. |
| 5,222,961 A | 6/1993 | Nakao et al. |
| 5,234,449 A | 8/1993 | Bruker et al. |
| 5,246,450 A | 9/1993 | Thornton et al. |
| 5,259,366 A | 11/1993 | Reydel et al. |
| 5,269,792 A | 12/1993 | Kovac et al. |
| 5,279,416 A | 1/1994 | Malec et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |

(56) References Cited

U.S. PATENT DOCUMENTS

| | | |
|---|---|---|
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,831 A | 6/1995 | Nates |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,564,262 A | 10/1996 | Bevis et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,582,616 A | 12/1996 | Bolduc et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,908,430 A | 6/1999 | Appleby |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |

(56) References Cited

U.S. PATENT DOCUMENTS

| | | |
|---|---|---|
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,158,583 A | 12/2000 | Forster |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,253 B1 | 8/2001 | Forster et al. |
| 6,273,898 B1 | 8/2001 | Kienzle et al. |
| 6,277,131 B1 | 8/2001 | Kalikow |
| 6,306,149 B1 | 10/2001 | Meade |
| 6,306,150 B1 | 10/2001 | Levinson |
| 6,318,619 B1 | 11/2001 | Lee |
| 6,322,571 B1 | 11/2001 | Adams |
| 6,349,727 B1 | 2/2002 | Stewart, Jr. |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,419,682 B1 | 7/2002 | Appleby et al. |
| 6,421,920 B1 | 7/2002 | Jensen |
| 6,423,079 B1 | 7/2002 | Blake, III |
| 6,428,548 B1 | 8/2002 | Durgin et al. |
| 6,439,727 B1 | 8/2002 | Koide |
| 6,440,144 B1 | 8/2002 | Bacher |
| 6,460,700 B2 | 10/2002 | Weisshaupt |
| 6,460,749 B1 | 10/2002 | Levinson et al. |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,863,675 B2 | 3/2005 | Wilson, Jr. |
| 6,869,435 B2 | 3/2005 | Blake, III |
| 6,869,436 B2 | 3/2005 | Wendlandt |
| 6,880,699 B2 | 4/2005 | Gallagher |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,001,412 B2 | 2/2006 | Gallagher et al. |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,131,977 B2 | 11/2006 | Fowler |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 * | 5/2007 | Hughett ............... A61B 17/068 606/143 |
| 7,213,736 B2 | 5/2007 | Wales et al. |
| 7,214,230 B2 | 5/2007 | Brock et al. |

(56) References Cited

U.S. PATENT DOCUMENTS

| | | |
|---|---|---|
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,452,368 B2 | 11/2008 | Liberatore et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,628,272 B2 | 12/2009 | Wiedenbein |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,129 B2 | 12/2010 | Taconi-Forrer et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,042,687 B2 | 10/2011 | Cannady |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,312,992 B2 | 11/2012 | Disch |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |

(56) References Cited

U.S. PATENT DOCUMENTS

| | | |
|---|---|---|
| 8,419,752 B2 | 4/2013 | Sorrentino et al. |
| 8,425,515 B2 | 4/2013 | Gamache et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,627,955 B2 | 1/2014 | Weisshaupt et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |
| 8,845,659 B2 | 9/2014 | Whitfield et al. |
| 8,888,398 B2 | 11/2014 | Werth |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,517,178 B2 | 12/2016 | Chancibot |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| D808,522 S | 1/2018 | Cannady et al. |
| 9,855,043 B2 | 1/2018 | Malkowski |
| 9,855,053 B2 | 1/2018 | Bagaoisan et al. |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,130,373 B2 | 11/2018 | Castro et al. |
| 10,136,898 B2 | 11/2018 | Schmidt et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,271,854 B2 | 4/2019 | Whitfield et al. |
| 10,292,712 B2 | 5/2019 | Shankarsetty |
| 10,349,936 B2 | 7/2019 | Rockrohr et al. |

(56) References Cited

U.S. PATENT DOCUMENTS

| | | |
|---|---|---|
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 10,470,765 B2 | 11/2019 | Malkowski |
| 10,485,538 B2 | 11/2019 | Whitfield et al. |
| 10,492,795 B2 | 12/2019 | Williams |
| 10,537,329 B2 | 1/2020 | Malkowski |
| 10,542,999 B2 | 1/2020 | Zergiebel |
| 10,548,602 B2 | 2/2020 | Baril et al. |
| 10,568,635 B2 | 2/2020 | Whitfield et al. |
| 10,582,931 B2 | 3/2020 | Mujawar |
| 10,603,038 B2 | 3/2020 | Mujawar et al. |
| 10,610,236 B2 | 4/2020 | Baril |
| 10,639,032 B2 | 5/2020 | Baril et al. |
| 10,639,044 B2 | 5/2020 | Prior |
| 10,653,429 B2 | 5/2020 | Baril et al. |
| 10,660,639 B2 | 5/2020 | Hartoumbekis |
| 10,660,651 B2 | 5/2020 | Baril et al. |
| 10,660,652 B2 | 5/2020 | Tan et al. |
| 10,660,723 B2 | 5/2020 | Baril |
| 10,660,725 B2 | 5/2020 | Baril et al. |
| 10,675,043 B2 | 6/2020 | P V R |
| 10,675,112 B2 | 6/2020 | Baril et al. |
| 10,682,135 B2 | 6/2020 | Sorrentino et al. |
| 10,682,146 B2 | 6/2020 | Rockrohr et al. |
| 10,702,278 B2 | 7/2020 | Tokarz et al. |
| 10,702,279 B2 | 7/2020 | Xu et al. |
| 10,702,280 B2 | 7/2020 | Cai et al. |
| 10,709,455 B2 | 7/2020 | Baril et al. |
| 10,722,235 B2 | 7/2020 | Baril et al. |
| 10,722,236 B2 | 7/2020 | Zammataro |
| 10,743,851 B2 | 8/2020 | Swayze et al. |
| 10,743,886 B2 | 8/2020 | Malkowski et al. |
| 10,743,887 B2 | 8/2020 | P V R |
| 10,758,234 B2 | 9/2020 | Malkowski et al. |
| 10,758,244 B2 | 9/2020 | Williams |
| 10,758,245 B2 | 9/2020 | Baril et al. |
| 10,765,431 B2 | 9/2020 | Hu et al. |
| 10,765,435 B2 | 9/2020 | Gokharu |
| 10,786,262 B2 | 9/2020 | Baril et al. |
| 10,786,263 B2 | 9/2020 | Baril et al. |
| 10,786,273 B2 | 9/2020 | Baril et al. |
| 10,806,463 B2 | 10/2020 | Hartoumbekis |
| 10,806,464 B2 | 10/2020 | Raikar et al. |
| 10,828,036 B2 | 11/2020 | Baril et al. |
| 10,828,044 B2 | 11/2020 | Gokharu |
| 10,835,260 B2 | 11/2020 | Baril et al. |
| 10,835,341 B2 | 11/2020 | Baril et al. |
| 10,849,630 B2 | 12/2020 | P V R |
| 10,863,992 B2 | 12/2020 | Czernik et al. |
| D907,200 S | 1/2021 | Baril et al. |
| D907,203 S | 1/2021 | Pilletere et al. |
| D907,204 S | 1/2021 | Pilletere et al. |
| 10,932,788 B2 | 3/2021 | Thomas et al. |
| 10,932,789 B2 | 3/2021 | Thomas et al. |
| 10,932,790 B2 | 3/2021 | Baril et al. |
| 10,932,791 B2 | 3/2021 | P V R |
| 10,932,793 B2 | 3/2021 | Yi et al. |
| 10,945,734 B2 | 3/2021 | Baril et al. |
| 10,959,737 B2 | 3/2021 | P V R |
| 10,993,721 B2 | 5/2021 | Baril et al. |
| 11,026,696 B2 | 6/2021 | Zammataro |
| 11,033,256 B2 | 6/2021 | Zammataro et al. |
| 11,051,827 B2 | 7/2021 | Baril et al. |
| 11,051,828 B2 | 7/2021 | Baril et al. |
| 11,058,432 B2 | 7/2021 | Bhatnagar et al. |
| 11,071,553 B2 | 7/2021 | Raikar et al. |
| 11,116,513 B2 | 9/2021 | Dinino et al. |
| 11,116,514 B2 | 9/2021 | Yue et al. |
| 11,134,956 B2 | 10/2021 | Shankarsetty |
| 11,147,566 B2 | 10/2021 | Pilletere et al. |
| 11,213,298 B2 | 1/2022 | Sorrentino et al. |
| 11,213,299 B2 | 1/2022 | Whitfield et al. |
| 2002/0046961 A1 | 4/2002 | Levinson et al. |
| 2002/0123742 A1 | 9/2002 | Baxter et al. |
| 2002/0177863 A1 | 11/2002 | Mandel et al. |
| 2003/0014060 A1 | 1/2003 | Wilson et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0199178 A1 | 10/2004 | Small |
| 2004/0230198 A1 | 11/2004 | Manzi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0165423 A1 | 7/2005 | Gallagher et al. |
| 2005/0165424 A1 | 7/2005 | Gallagher et al. |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0234478 A1 | 10/2005 | Wixey et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079115 A1 | 4/2006 | Aranyi |
| 2006/0085015 A1 | 4/2006 | Whitfield et al. |
| 2006/0085021 A1 | 4/2006 | Wenzler |
| 2006/0089659 A1 | 4/2006 | Small |
| 2006/0100649 A1 | 5/2006 | Hart |
| 2006/0124485 A1 | 6/2006 | Kennedy |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0149988 A1 | 6/2007 | Michler et al. |

(56) References Cited

U.S. PATENT DOCUMENTS

| | | |
|---|---|---|
| 2007/0149989 A1 | 6/2007 | Santilli et al. |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0171380 A1 | 7/2009 | Whiting |
| 2009/0182193 A1 | 7/2009 | Whitman et al. |
| 2009/0204115 A1 | 8/2009 | Dees, Jr. et al. |
| 2009/0209946 A1 | 8/2009 | Swayze et al. |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0057102 A1 | 3/2010 | Sorrentino et al. |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0028994 A1 | 2/2011 | Whitfield et al. |
| 2011/0054498 A1 | 3/2011 | Monassevitch et al. |
| 2011/0087220 A1 | 4/2011 | Felder et al. |
| 2011/0087268 A1 | 4/2011 | Livneh |
| 2011/0101066 A1 | 5/2011 | Farascioni et al. |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0295291 A1 | 12/2011 | Trivisani |
| 2011/0313437 A1 | 12/2011 | Yeh |
| 2012/0022526 A1 | 1/2012 | Aldridge et al. |
| 2012/0029534 A1 | 2/2012 | Whitfield |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0083803 A1 | 4/2012 | Patel et al. |
| 2012/0226291 A1 | 9/2012 | Malizia et al. |
| 2012/0234894 A1 | 9/2012 | Kostrzewski |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0245651 A1 | 9/2013 | Schmidt et al. |
| 2013/0253540 A1 | 9/2013 | Castro et al. |
| 2013/0261642 A1 | 10/2013 | Willett et al. |
| 2013/0325057 A1 | 12/2013 | Larson et al. |
| 2014/0005678 A1 | 1/2014 | Shelton, IV et al. |
| 2014/0025092 A1 | 1/2014 | Ewers et al. |
| 2014/0054192 A1 | 2/2014 | Chancibot |
| 2014/0074143 A1 | 3/2014 | Fitzgerald et al. |
| 2014/0131421 A1 | 5/2014 | Viola |
| 2014/0188159 A1 | 7/2014 | Steege |
| 2014/0236170 A1 | 8/2014 | Kethman et al. |
| 2014/0243862 A1 | 8/2014 | Bagaoisan et al. |
| 2014/0252065 A1 | 9/2014 | Hessler et al. |
| 2014/0263565 A1 | 9/2014 | Lytle, IV et al. |
| 2014/0276970 A1 | 9/2014 | Messerly et al. |
| 2014/0309677 A1 | 10/2014 | Baldwin |
| 2014/0324074 A1 | 10/2014 | Crainich et al. |
| 2014/0371728 A1 | 12/2014 | Vaughn |
| 2015/0032131 A1 | 1/2015 | Sorrentino et al. |
| 2015/0190133 A1 | 7/2015 | Penna et al. |
| 2015/0196298 A1 | 7/2015 | Menn et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2015/0327879 A1 | 11/2015 | Garrison et al. |
| 2016/0000428 A1 | 1/2016 | Scirica |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0151073 A1 | 6/2016 | Castro et al. |
| 2016/0166255 A1 | 6/2016 | Fischvogt |
| 2016/0192927 A1 | 7/2016 | Kostrzewski |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0249927 A1 | 9/2016 | Beckman et al. |
| 2016/0256157 A1 | 9/2016 | Rockrohr et al. |
| 2016/0256158 A1 | 9/2016 | Whitfield et al. |
| 2016/0296232 A1 | 10/2016 | Campbell |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2016/0354089 A1 | 12/2016 | Whiting |
| 2017/0020530 A1 | 1/2017 | Willett et al. |
| 2017/0027576 A1 | 2/2017 | Castro |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0165015 A1 | 6/2017 | Hess et al. |
| 2017/0172780 A1 | 6/2017 | Murthy Aravalli |
| 2017/0202567 A1 | 7/2017 | Griffiths et al. |
| 2017/0209151 A1 | 7/2017 | Brown |
| 2017/0238935 A1 | 8/2017 | Shi |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0036008 A1 | 2/2018 | Ramsey et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168659 A1 | 6/2018 | Bagaoisan et al. |
| 2018/0168660 A1 | 6/2018 | Gokharu |
| 2018/0185029 A1 | 7/2018 | Lebens, III |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |

(56) References Cited

U.S. PATENT DOCUMENTS

| | | |
|---|---|---|
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0271527 A1 | 9/2018 | Shellenberger |
| 2018/0271532 A1 | 9/2018 | Shellenberger |
| 2018/0271535 A1 | 9/2018 | Shellenberger et al. |
| 2018/0271536 A1 | 9/2018 | Shellenberger et al. |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046201 A1* | 2/2019 | Labhasetwar ...... A61B 17/1285 |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133590 A1 | 5/2019 | Richard |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0159782 A1 | 5/2019 | Kamaraj et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0223874 A1 | 7/2019 | Pilletere et al. |
| 2019/0239892 A1* | 8/2019 | Scott ...................... A61B 34/25 |
| 2019/0239893 A1 | 8/2019 | Shankarsetty |
| 2019/0247046 A1* | 8/2019 | Houser .............. A61B 17/1285 |
| 2019/0298377 A1 | 10/2019 | Castro |
| 2019/0314026 A1 | 10/2019 | Thomas et al. |
| 2019/0321047 A1 | 10/2019 | Thomas et al. |
| 2019/0321048 A1 | 10/2019 | Dinino et al. |
| 2019/0328391 A1 | 10/2019 | Holsten et al. |
| 2019/0328399 A1 | 10/2019 | Baril et al. |
| 2019/0357913 A1 | 11/2019 | Pilletere et al. |
| 2020/0008806 A1 | 1/2020 | Dinino et al. |
| 2020/0046329 A1 | 2/2020 | Baril et al. |
| 2020/0046359 A1 | 2/2020 | Thomas et al. |
| 2020/0046363 A1 | 2/2020 | Baril et al. |
| 2020/0046365 A1 | 2/2020 | Baril et al. |
| 2020/0046443 A1 | 2/2020 | Baril et al. |
| 2020/0060684 A1 | 2/2020 | Thomas et al. |
| 2020/0060686 A1 | 2/2020 | Williams |
| 2020/0113569 A1 | 4/2020 | Zergiebel |
| 2020/0129183 A1 | 4/2020 | Baril et al. |
| 2020/0146687 A1 | 5/2020 | Whitfield et al. |
| 2020/0170646 A1 | 6/2020 | Mujawar |
| 2020/0229825 A1 | 7/2020 | P V R |
| 2020/0261095 A1 | 8/2020 | Yi et al. |
| 2020/0315629 A1 | 10/2020 | Xu et al. |
| 2020/0405315 A1 | 12/2020 | Zhang et al. |
| 2021/0000474 A1 | 1/2021 | Thomas et al. |
| 2021/0030420 A1 | 2/2021 | Pilletere et al. |
| 2021/0030421 A1 | 2/2021 | Baril et al. |
| 2021/0038225 A1 | 2/2021 | Baril et al. |
| 2021/0059681 A1 | 3/2021 | Zhang et al. |
| 2021/0169482 A1 | 6/2021 | Baril et al. |
| 2021/0204946 A1 | 7/2021 | Banerjee et al. |
| 2021/0298758 A1 | 9/2021 | Thomas et al. |
| 2021/0401438 A1 | 12/2021 | Pilletere et al. |

FOREIGN PATENT DOCUMENTS

| | | |
|---|---|---|
| CA | 1163889 A | 3/1984 |
| CN | 101164502 A | 4/2008 |
| CN | 202699217 U | 1/2013 |
| CN | 103251441 A | 8/2013 |
| CN | 204839635 U | 12/2015 |
| CN | 106264647 A | 1/2017 |
| CN | 104605911 B | 2/2017 |
| DE | 29520789 U1 | 6/1996 |
| DE | 10116168 A1 | 11/2001 |
| DE | 202005001664 U1 | 5/2005 |
| DE | 202007003398 U1 | 6/2007 |
| EP | 0000756 A1 | 2/1979 |
| EP | 0406724 A1 | 1/1991 |
| EP | 0514139 A2 | 11/1992 |
| EP | 0576835 A2 | 1/1994 |
| EP | 0732078 A2 | 9/1996 |
| EP | 1769757 A1 | 4/2007 |
| EP | 3046482 A1 | 7/2016 |
| EP | 3132756 A1 | 2/2017 |
| EP | 3305217 A1 | 4/2018 |
| EP | 3400887 A1 | 11/2018 |
| EP | 3476331 A1 | 5/2019 |
| EP | 3552560 A1 | 10/2019 |
| EP | 3572012 A1 | 11/2019 |
| GB | 2073022 A | 10/1981 |
| GB | 2353710 A | 3/2001 |
| JP | 06054858 | 3/1994 |
| JP | 2003033361 A | 2/2003 |
| JP | 2006154230 A | 6/2006 |
| JP | 2006277221 A | 10/2006 |
| JP | 2008017876 A | 1/2008 |
| JP | 2008200190 A | 9/2008 |
| JP | 2011186812 A | 9/2011 |
| JP | 2013166982 A | 8/2013 |
| WO | 9003763 A1 | 4/1990 |
| WO | 9624294 A1 | 8/1996 |
| WO | 0042922 A1 | 7/2000 |
| WO | 0166001 A2 | 9/2001 |
| WO | 0167965 A1 | 9/2001 |
| WO | 2013040306 A1 | 3/2013 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |
| WO | 2018035796 A1 | 3/2018 |

OTHER PUBLICATIONS

International Search Report and Written Opinion corresponding to International Application No. PCT/US18/050325 mailed Jan. 7, 2019.

International Search Report and Written Opinion corresponding to International Application No. PCT/US2018/057922 mailed Feb. 22, 2019.

Chinese First Office Action corresponding to Patent Application CN 201610055870.8 dated Aug. 1, 2019.

Japanese Office Action corresponding to Patent Application JP 2015-203499 dated Aug. 16, 2019.

Chinese Second Office Action corresponding to Patent Application CN 201510696298.9 dated Aug. 21, 2019.

Japanese Office Action corresponding to Patent Application JP 2018-516433 mailed Aug. 21, 2019.

Chinese First Office Action corresponding to Patent Application CN 201580072284.8 dated Aug. 29, 2019.

Chinese First Office Action corresponding to Patent Application CN 201580073962.2 dated Sep. 5, 2019.

(56) References Cited

OTHER PUBLICATIONS

Extended European Search Report corresponding to Patent Application EP 19151805.9 dated Sep. 5, 2019.
Japanese Office Action corresponding to Patent Application JP 2018-537512 mailed Sep. 9, 2019.
Extended European Search Report corresponding to Patent Application EP 19170951.8 dated Sep. 26, 2019.
Extended European Search Report corresponding to Patent Application EP 15908020.9 dated Oct. 9, 2019.
Japanese Office Action corresponding to Patent Application JP 2018-534822 mailed Oct. 17, 2019.
Extended European Search Report corresponding to Patent Application EP 16884297.9 dated Oct. 31, 2019.
Extended European Search Report corresponding to Patent Application EP 16885490.9 dated Nov. 12, 2019.
Extended European Search Report corresponding to Patent Application EP 19191203.9 dated Dec. 9, 2019.
Extended European Search Report corresponding to Patent Application EP 19191226.0 dated Dec. 10, 2019.
Extended European Search Report corresponding to Patent Application EP 19172130.7 dated Dec. 19, 2019.
European Office Action corresponding to Patent Application EP 18 187 690.5 dated Mar. 23, 2020.
Extended European Search Report corresponding to Patent Application EP 16912243.9 dated Mar. 25, 2020.
Chinese First Office Action corresponding to Patent Application CN 201610694951.2 dated Apr. 23, 2020.
Partial Supplementary European Search Report corresponding to Patent Application EP 18899075.8 dated Jul. 1, 2021.
Australian Examination Report No. 1 corresponding to Patent Application AU 2015413639 dated Jul. 23, 2020.
Chinese First Office Action corresponding to Patent Application CN 201680078525.4 dated Jul. 28, 2020.
Japanese Office Action corresponding to Patent Application JP 2016-217970 dated Sep. 28, 2020.
Extended European Search Report corresponding to Patent Application EP 17895153.9 dated Dec. 17, 2020.
Extended European Search Report corresponding to Patent Application EP 20215391.2 dated Apr. 30, 2021.
Extended European Search Report corresponding to Patent Application EP 18873112.9 dated Oct. 18, 2021.
Extended European Search Report corresponding to Patent Application EP 21164196.4 dated Dec. 17, 2021.
Canadian Office Action dated Sep. 6, 2016 corresponding to Patent Application CA 2,728,538.
Japanese Office Action mailed Sep. 1, 2014 corresponding to counterpart Patent Application JP 2011-039024.
Extended European Search Report dated Dec. 17, 2021, issued in corresponding EP Application 21164196, 12 pages.
Chinese International PCT Application No. PCT/CN2018/078294 filed Mar. 7, 2018, Covidien LP.

* cited by examiner

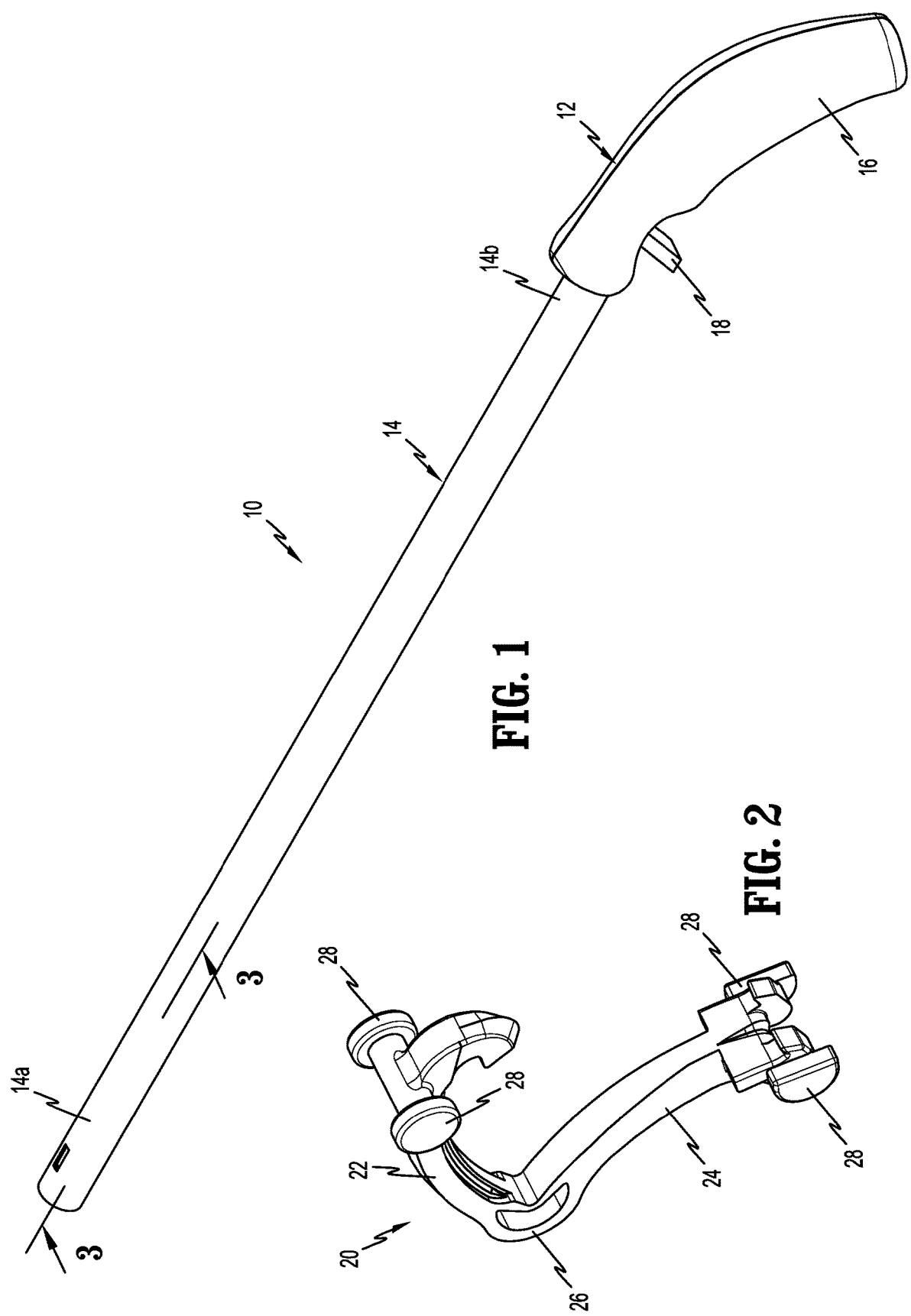

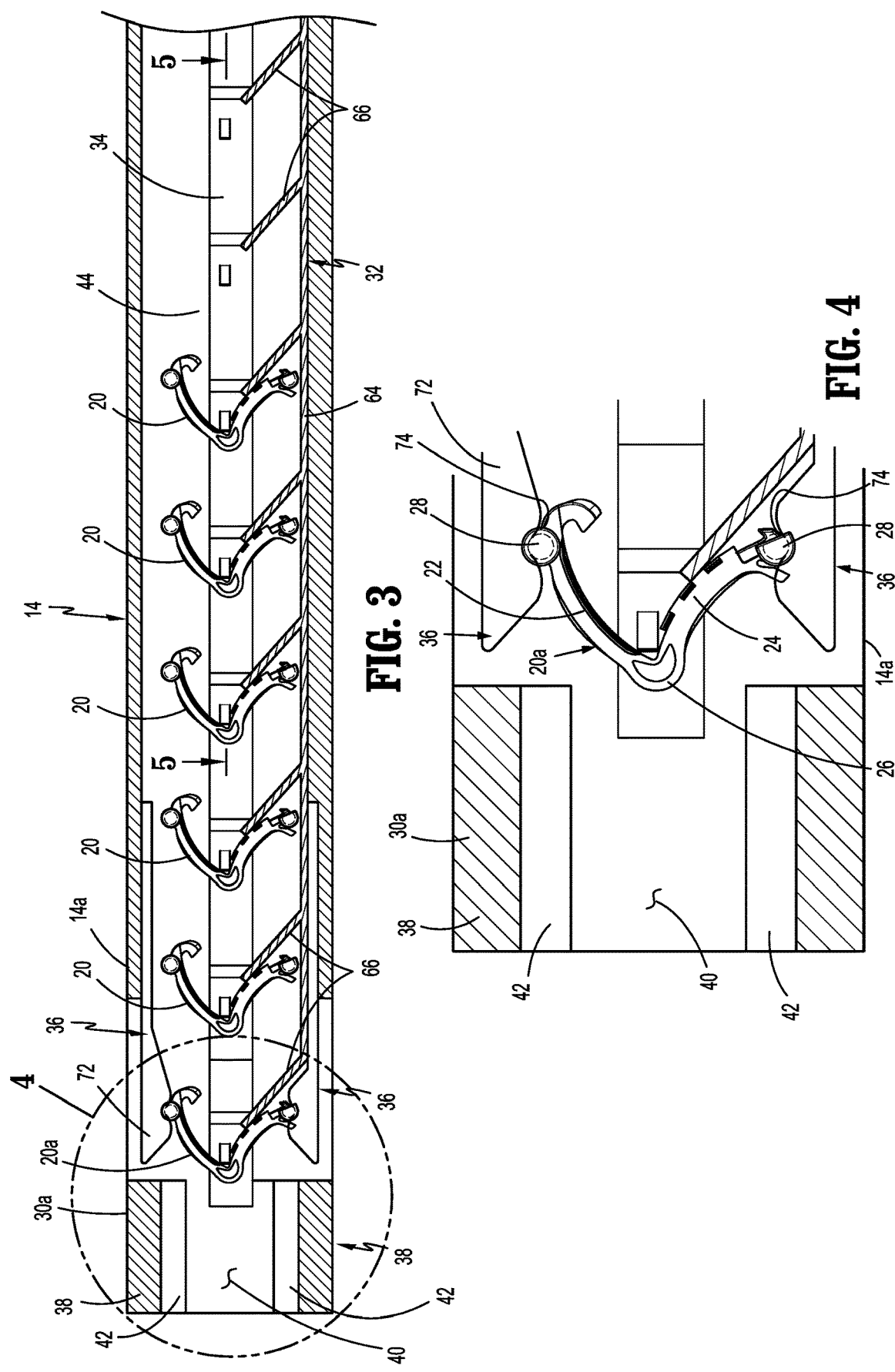

INTEROPERATIVE CLIP LOADING DEVICE

CROSS-REFERENCE TO RELATED APPLICATION

This application claims the benefit of and priority to U.S. Provisional Patent Application Ser. No. 63/000,091, filed Mar. 26, 2020, which is incorporated by reference herein in its entirety.

FIELD

This technology is generally related to surgical clip appliers and, more particularly, to a clip loading device for intraoperatively loading ligation clips into a ligation clip applier.

BACKGROUND

Endoscopic ligation clip appliers are used to apply ligation clips to body vessels during surgical procedures to occlude or partially occlude the body vessels. These clip appliers are inserted through small diameter cannulas or small incisions in a patient's body to access a surgical site within a body cavity. Performing a surgical procedure endoscopically reduces the amount of trauma inflicted on a patient during a surgical procedure to minimize patient discomfort and reduce patient recovery times.

Surgical clip appliers include single-fire clip appliers and multi-fire clip appliers. In single-fire clip appliers, a ligation clip is loaded into the clip applier after each use. Typically, the clip applier is used to withdraw a single clip from a clip package to load the clip into jaws of the clip applier prior to each use of the clip applier. During an endoscopic procedure in which a single-fire clip applier is used, the clip applier is removed from a body cavity after each use to reload a ligation clip into the clip applier. This process is time consuming and increases the possibility of infection, thus increasing trauma to the patient.

Multi-fire clip appliers include a clip cartridge that is coupled to an elongate body of the clip applier that includes a plurality of ligation clips that are sequentially supplied to the jaws of the clip applier to facilitate placement of multiple clips on a body vessel or on body vessels without withdrawing the clip applier from within a body cavity. These clip appliers are complex especially where articulation of the distal portion of the clip applier is desired.

SUMMARY

This disclosure is directed to a clip loading device for a clip applier. The clip loading device includes an elongate body that can be positioned at a surgical site during an endoscopic surgical procedure to provide a supply of ligation clips to the clip applier.

Aspects of this disclosure are directed to an intraoperative clip loading device including a handle assembly, an elongate body, a guide member, clip retainers, a plurality of ligation clips, clip locking arms, and a clip advancing member. The handle assembly includes a handle grip. The elongate body has a proximal portion and a distal portion and defines a longitudinal axis. The proximal portion is coupled to the handle assembly. The elongate body includes an outer tube having a distal portion defining an opening and including an inner wall. The guide member is positioned on the distal portion of the outer tube and includes diametrically opposed channels that are configured to receive jaws of a clip applier. The clip retainers are supported on the inner wall of the outer tube and define clip retention pockets positioned along the longitudinal axis of the elongate body. Each of the plurality of ligation clips is supported within one of the clip retention pockets and includes a first beam, a second beam, and a hinge portion coupling the first beam to the second beam. Each of the first and second beams includes spaced bosses. The clip locking arms are supported within the distal portion of the outer tube and are formed of a resilient material. The clip locking arms are aligned with the opposed channels in the guide member and include concavities configured to receive the spaced bosses of a respective one of the first and second beams of the ligation clips. The clip advancing member includes an elongate member and a plurality of resilient fingers. Each of the resilient fingers engages a respective one of the plurality of ligation clips. The clip advancing member is movable within the outer tube from a retracted position to an advanced position to move the plurality of clips distally within the outer tube.

Other aspects of the disclosure are directed to an intraoperative clip loading device including an elongate body, clip retainers, a plurality of ligation clips, clip locking arms, and a clip advancing member. The elongate body has a proximal portion and a distal portion and defines a longitudinal axis. The elongate body includes an outer tube having a distal portion defining an opening and including an inner wall. The clip retainers are supported on the inner wall of the outer tube and define clip retention pockets along the longitudinal axis of the elongate body. Each of the longitudinal portions includes a flexible tab having a stop surface. Each of the plurality of ligation clips is supported within one of the clip retention pockets and includes a first beam, a second beam, and a hinge portion coupling the first beam to the second beam. Each of the first and second beams includes spaced bosses. The stop surfaces of the flexible tabs of the clip retainers are positioned to engage the hinge portions of the plurality of ligation clips to prevent proximal movement of the plurality of ligation clips within the outer tube. The clip locking arms are supported within the distal portion of the outer tube and are formed of a resilient material. The clip locking arms are aligned with the opposed channels in the guide member and include concavities configured to receive the spaced bosses of a respective one of the first and second beams of the ligation clips. The clip advancing member includes an elongate member and a plurality of resilient fingers. Each of the resilient fingers engages a respective one of the plurality of ligation clips. The clip advancing member is movable within the outer tube from a retracted position to an advanced position to move the plurality of clips distally within the outer tube.

Other aspects of the disclosure are directed to an intraoperative clip loading device including a handle assembly, an elongate body, clip retainers, a plurality of ligation clips, clip locking arms, and a clip advancing member. The handle assembly includes a handle grip and an actuator. The elongate body has a proximal portion and a distal portion and defines a longitudinal axis. The proximal portion is coupled to the handle assembly. The elongate body includes an outer tube having a distal portion defining an opening and an inner wall. The clip retainers are supported on the inner wall of the outer tube and define clip retention pockets positioned along the longitudinal axis of the elongate body. The clip retainers are formed of a resilient material. Each of the clip retainers includes a base portion secured to the inner wall of the outer tube and a longitudinal portion. The clip retainers are positioned along opposite sides of the outer tube and each of the clip retainers is aligned with another of the clip retainers such that two diametrically opposed clip retainers cooperate to define one of the clip retention pockets. Each of the plurality of ligation clips is supported within one of the clip retention pockets and includes a first beam, a second beam, and a hinge portion that couples the first beam to the second beam. Each of the first and second beams includes spaced bosses. The clip locking arms are supported within the distal portion of the outer tube and are formed of a resilient material. The clip locking arms are aligned with the opposed channels in the guide member and include a concavity that is configured to receive the spaced bosses of a respective one of the first and second beams of the ligation clips. The clip advancing member includes an elongate member and a plurality of resilient fingers. Each resilient finger of the plurality of resilient fingers engages a respective one of the plurality of ligation clips. The clip advancing member is movable within the outer tube from a retracted position to an advanced position in response to actuation of the actuation member to move the plurality of clips distally within the outer tube.

In aspects of the disclosure, the handle assembly includes an actuator that is movable to move the clip advancing member between its retracted and advanced positions.

In some aspects of the disclosure, the clip retainers are formed of a resilient material.

In certain aspects of the disclosure, each of the clip retainers includes a base portion secured to the inner wall of the outer tube and a longitudinal portion, and the clip retainers are positioned along opposite sides of the outer tube in alignment with another of the clip retainers such that two diametrically opposed clip retainers cooperate to define one of the clip retention pockets.

In aspects of the disclosure, each of the clip retainers includes a transverse portion that interconnects the base portion and the longitudinal portion.

In some aspects of the disclosure, each of the longitudinal portions includes a flexible tab that is positioned to engage the hinge portion of a respective one of the plurality of ligation clips to prevent proximal movement of the respective ligation clip within the outer tube.

In certain aspects of the disclosure, each of the flexible tabs is secured to the longitudinal portion of a respective one of the clip retainers in cantilevered fashion and includes a distal stop surface.

In aspects of the disclosure, the clip locking arms are secured to the inner wall of the outer tube in cantilevered fashion, and each of the clip locking arms includes a proximal portion and a distal portion, wherein the concavities are formed in the distal portion of the clip locking members.

In some aspects of the disclosure, the outer tube defines cutouts that are aligned with the distal portions of the clip locking arms, and the distal portions of the clip locking arms are deflectable outwardly into the cutouts to receive one of the plurality of ligation clips.

In certain aspects of the disclosure, the resilient fingers of the clip advancing members extend inwardly in a distal direction from the elongate member of the clip advancing members into engagement with one of the first and second beams of a respective one of the plurality of ligation clips.

Another aspect of the disclosure is directed to a method of intraoperatively loading a ligation clip into a clip applier which includes inserting the clip applier through a first incision in a patient to access a body cavity of the patient; inserting a clip loading device which supports a plurality of ligation clips through a second incision in the patient to access the body cavity; and inserting a jaw assembly of the clip applier into the clip loading device within the body cavity to load a first ligation clip of the plurality of ligation clips from the clip loading device into the jaw assembly of the clip applier.

In aspects of the disclosure the method includes applying a ligation clip to tissue within the body cavity of the patient and subsequently inserting the jaw assembly of the clip applier into the clip loading device to load a second ligation clip of the plurality of ligation clips from the clip loading device into the jaw assembly of the clip applier Other features of the disclosure will be appreciated from the following description.

BRIEF DESCRIPTION OF DRAWINGS

Various aspects of the disclosed intraoperative ligation clip loading device are described herein below with reference to the drawings, wherein:

FIG. 1 is a side perspective view of an intraoperative ligation clip loading device according to aspects of the present disclosure;

FIG. 2 is a side perspective view of an exemplary ligation clip of the intraoperative ligation clip loading device shown in FIG. 1;

FIG. 3 is a cross-sectional view of a distal portion an elongate body of the intraoperative ligation clip loading device taken along section line 3-3 of FIG. 1 including a plurality of ligation clips;

FIG. 4 is an enlarged view of the indicated area of detail shown in FIG. 3;

FIG. 8A is a side perspective view of the intraoperative ligation clip loading device shown in FIG. 1 with a ligation clip applier positioned adjacent a distal portion of the loading device;

DETAILED DESCRIPTION

Figure 5:
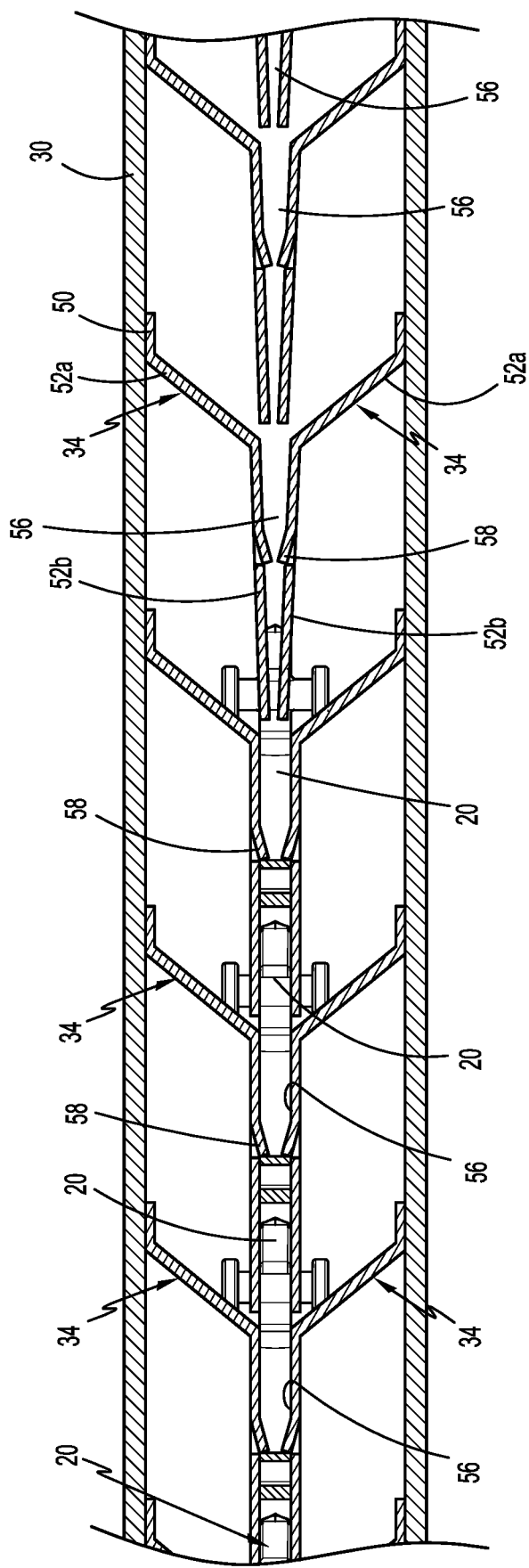
FIG. 5 is a cross-sectional, cutaway view of a central portion of the elongate body of the intraoperative ligation clip loading device shown in FIG. 1 including a plurality of ligation clips.
Figure 5A:
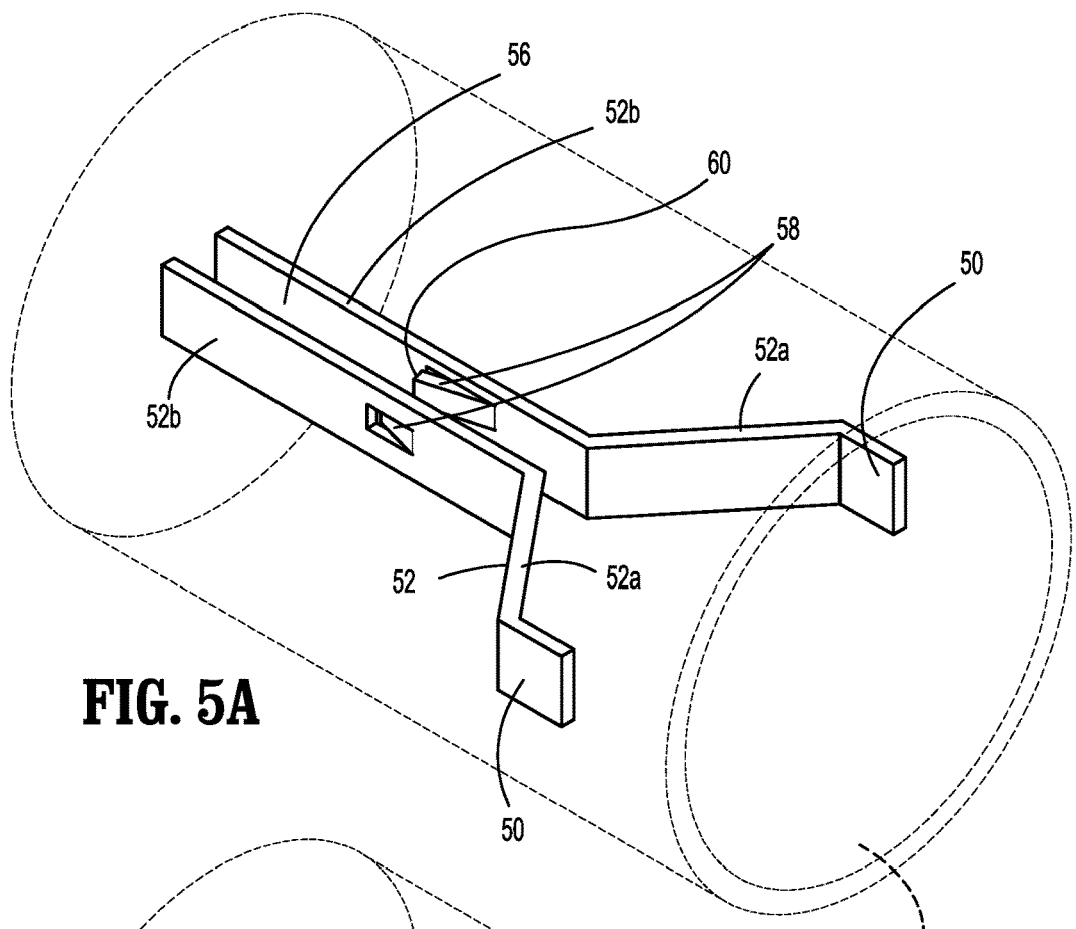
FIG. 5A is a side perspective view of clip retainers supported within a portion of the elongate body of the intraoperative ligation clip loading device shown in FIG. 1 with the portion of the elongate body shown in phantom.

The disclosed intraoperative clip loading device will now be described in detail with reference to the drawings in which like reference numerals designate identical or corresponding elements in each of the several views. However, it is to be understood that aspects of the disclosure included herein are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "endoscopic" is used generally to refer to endoscopic, laparoscopic, arthroscopic, and/or any other procedure conducted through a small diameter incision or cannula. Further, the term "clinician" is used generally to refer to medical personnel including doctors, nurses, and support personnel.

The disclosed intraoperative clip loading device includes an elongate body that supports a plurality of ligation clips and a clip advancing member for advancing the plurality of ligation clips towards a distal portion of the elongate body. The distal portion of the elongate body defines an opening that is accessible to a ligation clip applier to facilitate loading of the ligation clip applier through the distal portion of the elongate body of the intraoperative clip loading device. The elongate body is dimensioned to be positioned through a standard size port of a cannula to access a surgical site. The loading device can be positioned within a body cavity during an endoscopic surgical procedure to facilitate intraoperative loading of the ligation clip applier in vivo.

FIG. 1 illustrates exemplary aspects of the disclosed intraoperative clip loading device shown generally as loading device 10. The loading device 10 includes a handle assembly 12 and an elongate body 14. The elongate body 14 includes a distal portion 14a and a proximal portion 14b that is fixedly coupled to the handle 12. The handle assembly 12 includes a handle grip 16 and an actuator 18. Although the handle grip 16 is illustrated as a pistol-type grip, it is envisioned that the handle grip 16 may have a variety of configurations that are ergonomically pleasing to a clinician.

Figure 8:
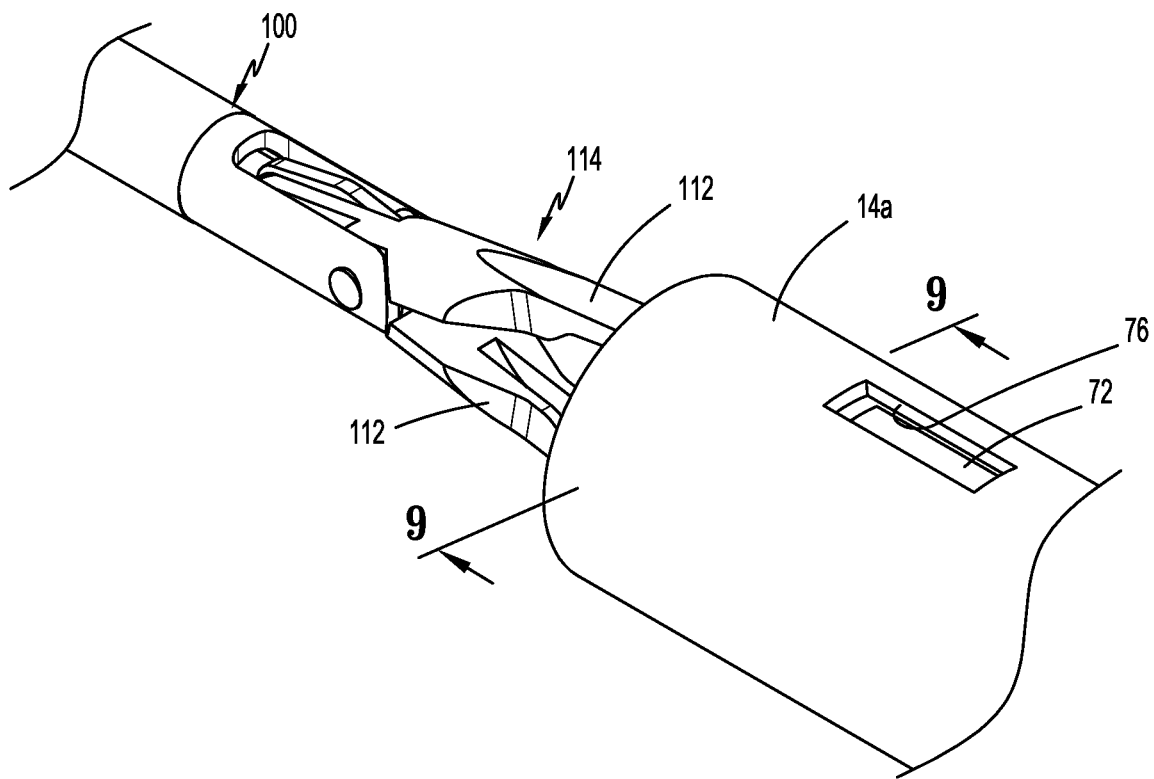
FIG. 8 is a side perspective view of the distal portion of the intraoperative ligation clip loading device shown in FIG. 8A as the ligation clip applier is inserted into the distal portion of the intraoperative ligation clip loading device.
Figure 9:
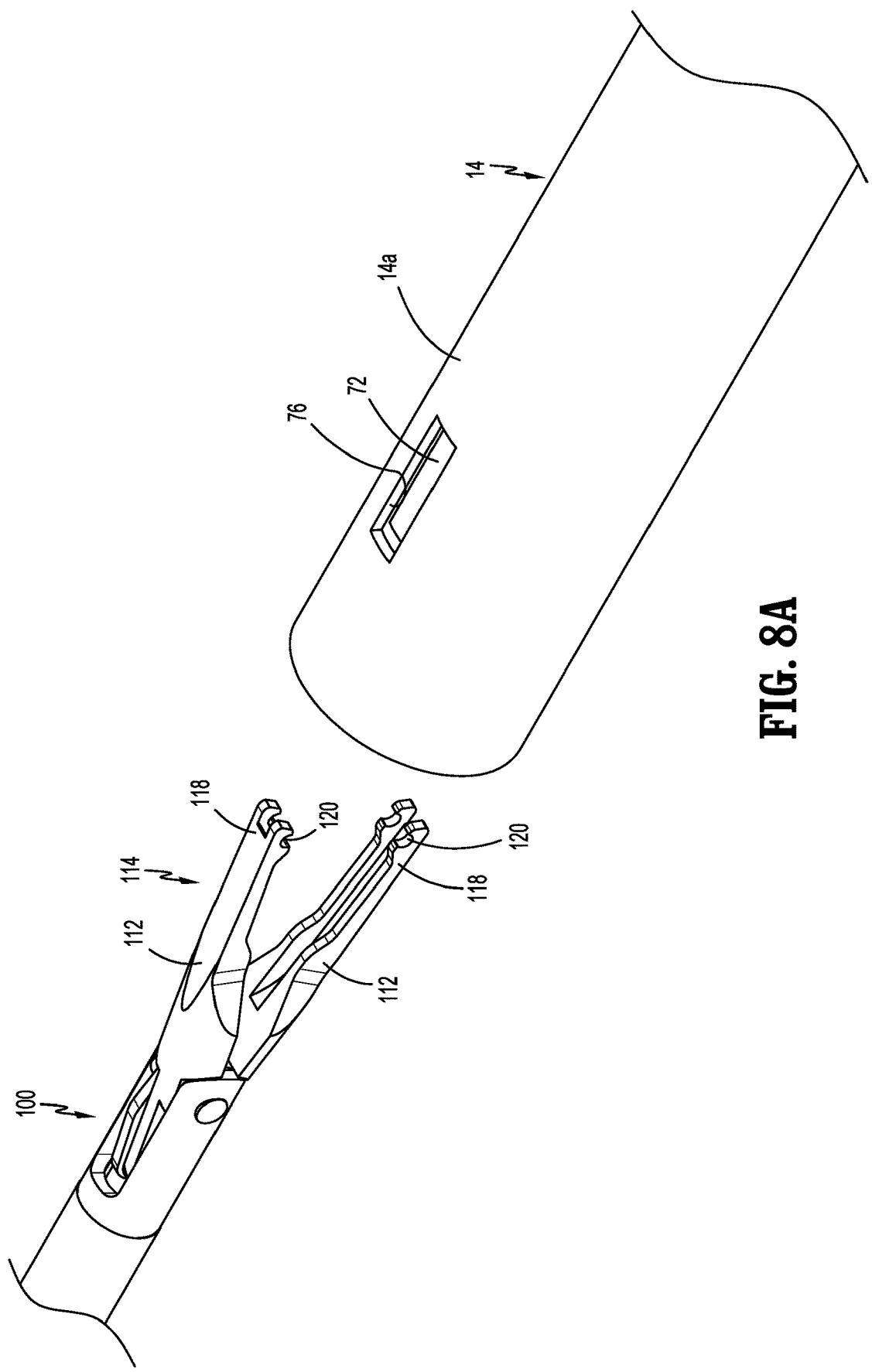
FIG. 9 is a cross-sectional view taken along section line 9-9 of FIG. 8 illustrating the ligation clip applier positioned within the distal portion of the intraoperative ligation clip loading device.
Figure 10:
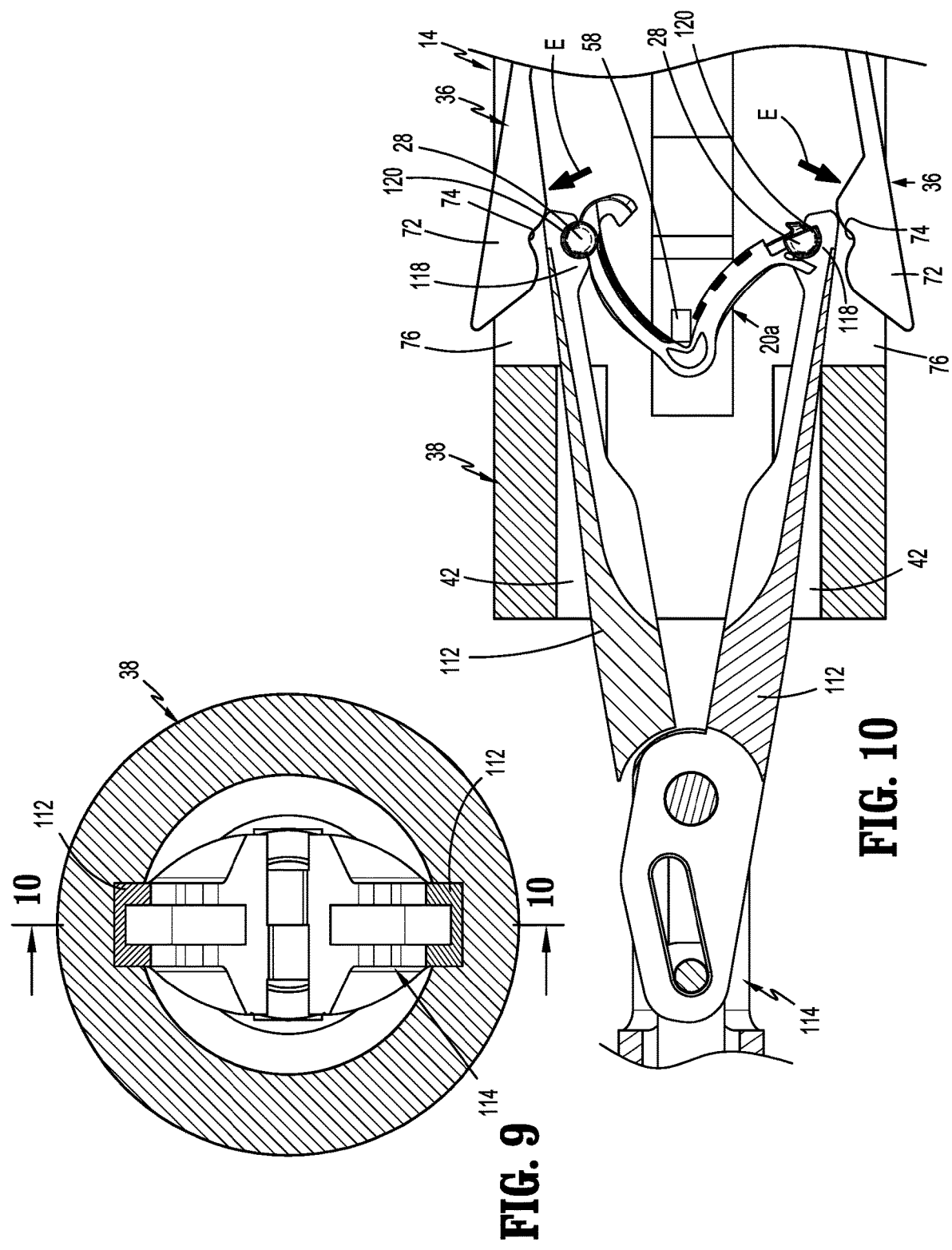
FIG. 10 is a cross-sectional view taken along section line 10-10 of FIG. 9.
Figure 11:
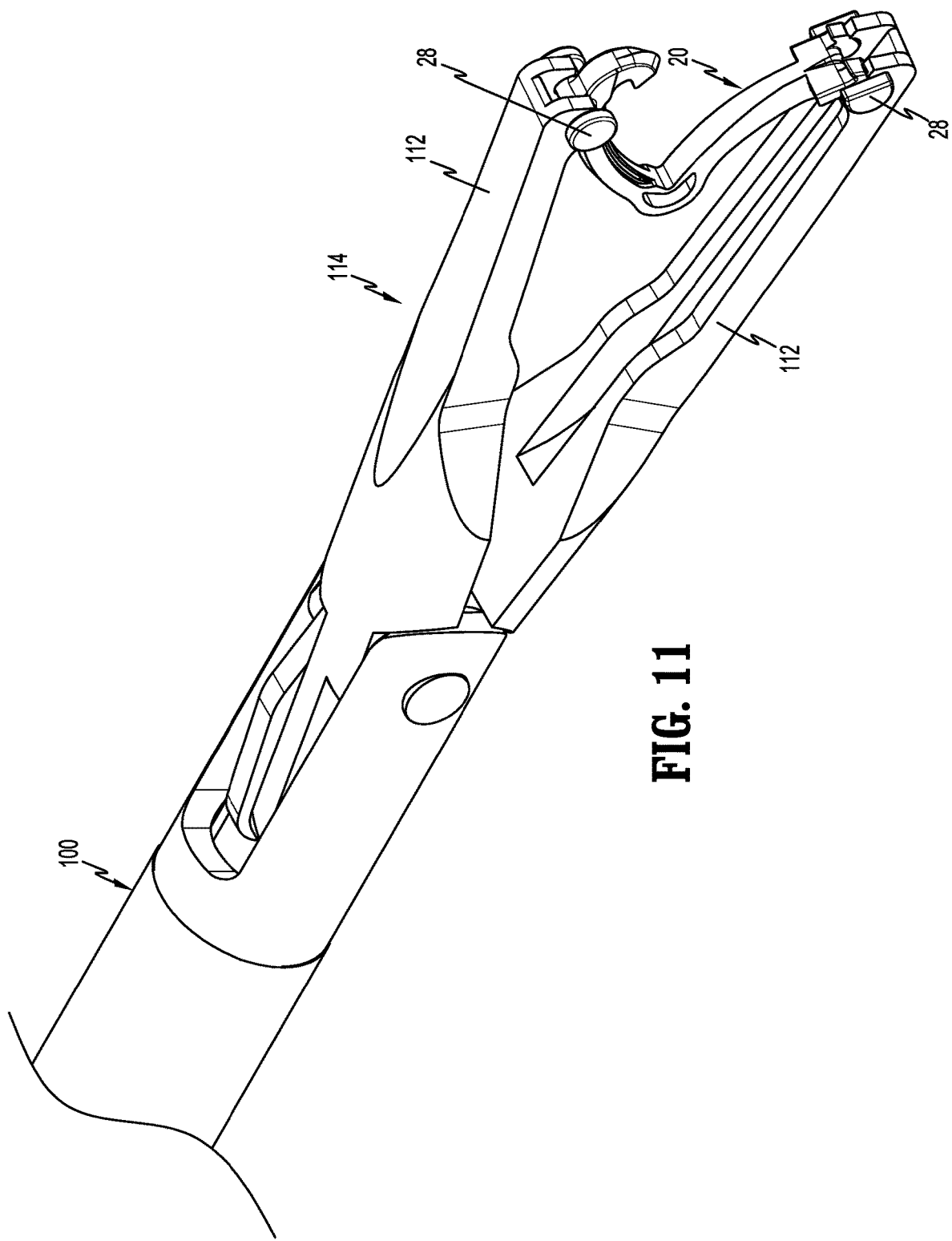
FIG. 11 is a side perspective view from a distal end of a ligation clip applier supporting a ligation clip removed from the distal portion of the intraoperative ligation clip loading device.
Figure 12:
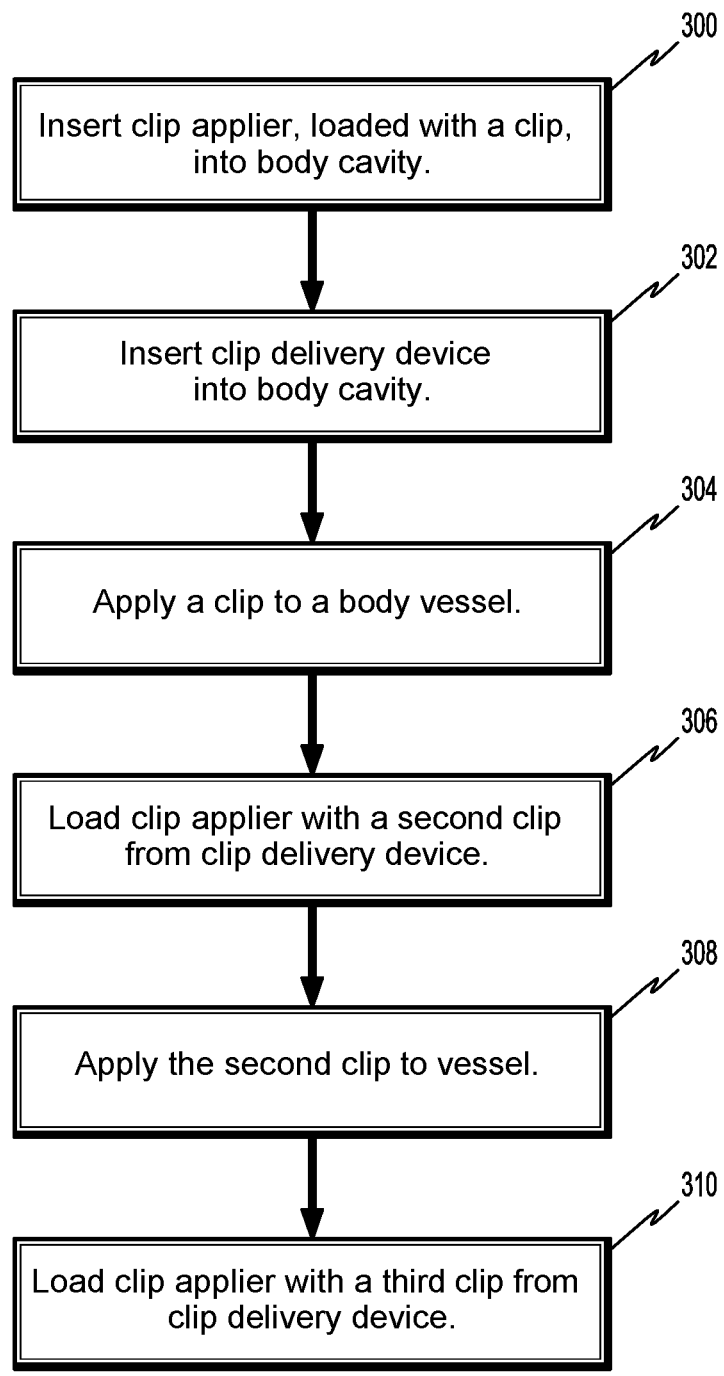
FIG. 12 is a flowchart of the method for using the intraoperative clip loading device shown in FIG. 1.
Figure 13:
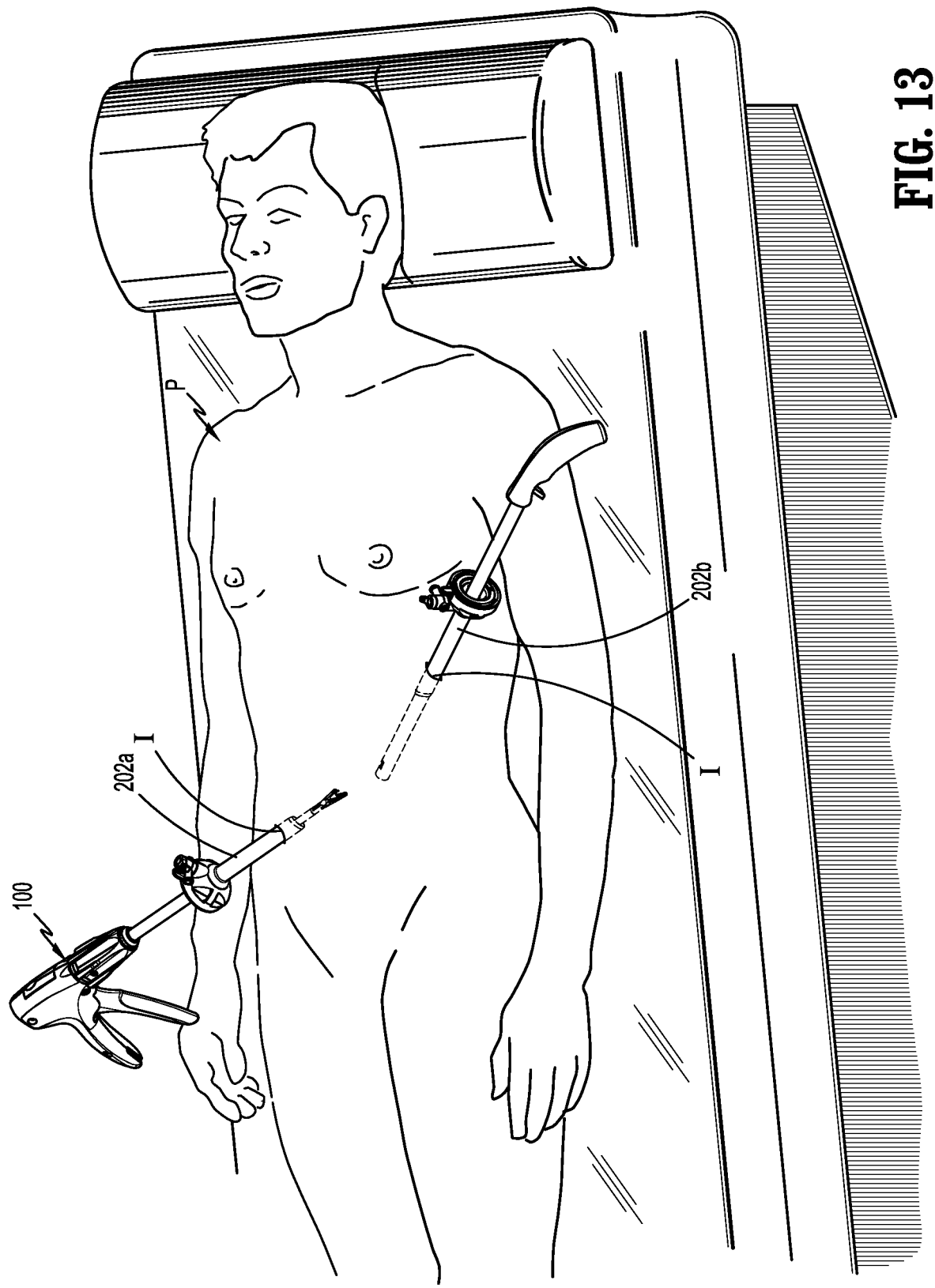
FIG. 13 is a perspective view of a patient with the intraoperative device shown in FIG. 1 and the clip applier shown in FIG. 11 positioned within a patient.

FIG. 2 illustrates a ligation clip 20, a plurality of which is received within the elongate body 14 of the loading device 10. Each of the ligation clips 20 includes a first beam 22, a second beam 24, and a hinge portion 26 that interconnects the first beam 22 to the second beam 24 and allows the ligation clip 20 to pivot between open and clamped positions. Each of the beams includes bosses 28 that are positioned on opposite sides of the respective beams 22 and 24. The bosses 28, as known in the art, provide engagement surfaces that facilitate securement of the ligation clip 20 onto to a ligation clip applier 100 (FIG. 8A).

FIGS. 3-5B illustrate the elongate body 14 of the loading device 10 which includes an outer tube 30, a clip advancing member 32, clip retainers 34, clip locking arms 36, and a guide member 38. The outer tube 30 is hollow and houses each of the components of the elongate body 14 listed above as well as a plurality of ligation clips 20. The outer tube 30 includes a distal portion 30a that receives or supports the guide member 38. In aspects of the disclosure, the outer tube 30 and the guide member 38 are integrally formed although it is envisioned that the guide member 38 could be formed separately from the outer tube 30 and secured to the outer tube 30. The guide member 38 defines a through bore 40 and includes diametrically opposed rectangular guide channels 42 that extend from the outwardly from the through bore 40. The guide channels 42 receive jaws 112 (FIG. 8A) of an end effector 114 of a clip applier 100 to guide the jaws 112 into engagement with a distal-most clip 20a of the plurality of clips 20 supported within the outer tube 30 as described in further detail below.

Figure 5B:
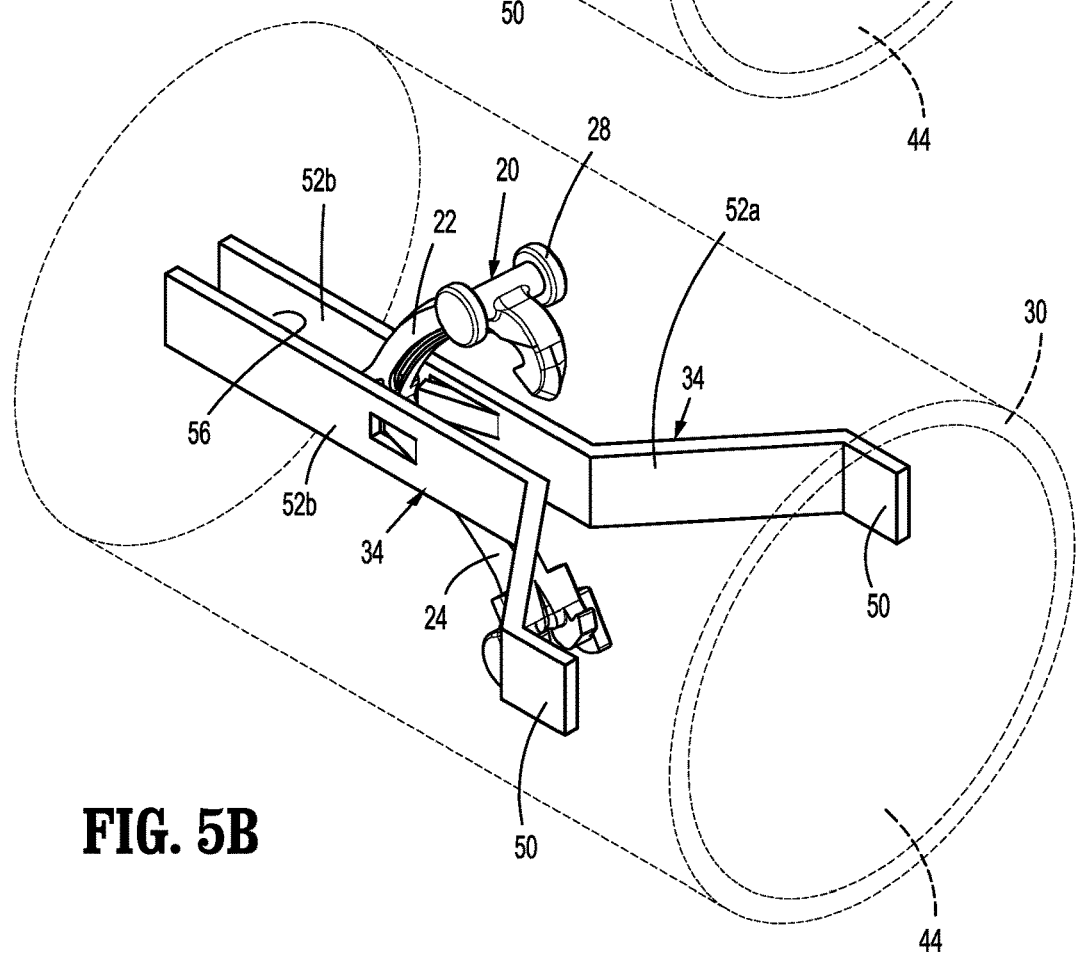
FIG. 5B is a side perspective view of the clip retainers supported within a portion of the elongate body of the intraoperative ligation clip loading device shown in FIG. 1 with the portion of the elongate body shown in phantom and a clip supported between the clip retainers.

The clip retainers 34, best shown in FIGS. 5-5B, are formed of a resilient material and include a base portion 50 and flexible arms 52. The flexible arms 52 extend from the base portion and include a transverse portion 52a and a longitudinal portion 52b. The base portion 50 of each of the clip retainers 34 is secured to an inner wall 44 of the outer tube 30. Each of the clip retainers 34 is positioned in opposition to another one of the clip retainers 34 to define a clip retention pocket 56 between the two opposed clip retainers 34. The clip retention pockets 56 are defined between respective opposed clip retainers 34 along the outer tube 30 from a proximal end portion of the outer tube 30 to a distal end portion of the outer tube 30. When a ligation clip 20 is received between the longitudinal portions 52b of the two opposed clip retainers 34, the flexible arms 52 of the clip retainers 34 flex outwardly and apply an inwardly directed force onto the hinge portion 26 and beams 22 and 24 of the ligation clip 20 to support the ligation clip 20 within the outer tube 30 of the elongate body 14 of the loading device 10 (FIG. 5B).

Each of the longitudinal portions 52b of the flexible arms 52 of the clip retainers 34 includes a flexible tab 58 that has a proximal end that is secured to the flexible arm 52 in cantilevered fashion and a distal end that defines a distal stop surface 60. When a ligation clip 20 is received between the flexible arms 52, the tabs 58 are deformed inwardly to allow the ligation clip 20 to move distally by the tab 58. When the ligation clip 20 moves past the tab 58, the tab 58 springs outwardly such that the stop surface 60 of the tab 58 is aligned with the hinge portion 26 of a respective one of the ligation clips 20 to obstruct proximal movement of the ligation clip 20 within the outer tube 30.

FIGS. 3 and 4 illustrate the clip advancing member 32 which is movable within the outer tube 30 between retracted and advanced positions and includes an elongate member 64 and a plurality of resilient fingers 66. Each of the plurality of resilient fingers 66 extends from the elongate member 64 in a distal direction at an acute angle into the outer tube 30 and engages the second beam 24 of one of the ligation clips 20. The elongate member 64 has a proximal portion (not shown) that is coupled to the actuator 18 of the handle assembly 12 such that actuation of the actuator 18 moves the clip advancing member 32 between its retracted and advanced positions. When the clip advancing member 32 is moved from its retracted position to its advanced position, each of the ligation clips 20 is advanced within the outer tube 30 from a first retention pocket 56 between two opposed clip retainers 34 to the next distally located retention pocket 56 within the outer tube 30.

The clip locking arms 36 are secured in cantilevered fashion within the distal portion of the outer tube 30 and are formed of a resilient material. Each of the clip locking arms 36 has a proximal portion 70 that is secured to the inner wall 44 of the outer tube 30 and a distal portion 72 that includes a concavity 74. The concavities 74 of the clip locking arms 36 receive the bosses 28 of a respective ligation clip 20 when the ligation clip 20 is delivered to a position between the clip locking arms 36 by the clip advancing member 32. The distal portion 72 of each of the clip locking arms 36 is positioned adjacent to a cutout 76 formed in the outer tube 30 of the elongate body 14. The cutouts 76 accommodate the distal portions of the clip locking arms 36 as a ligation clip 30 is advanced to a position between the clip locking arms 36. More specifically, the cutouts 76 allow the clip locking arms 36 to flex outwardly when a ligation clip 20 is delivered to the clip locking arms 36 by the clip advancing member 32 and when a ligation clip 20 is removed from the elongate body 14 by a clip applier 100 (FIG. 8A) as described in further detail below. The clip locking arms 36 are longitudinally aligned with guide channels 42 formed in the guide member 38 and with the clip retention pockets 56 defined by the clip retainers 34 positioned along the length of the outer tube 30.

Figure 6:
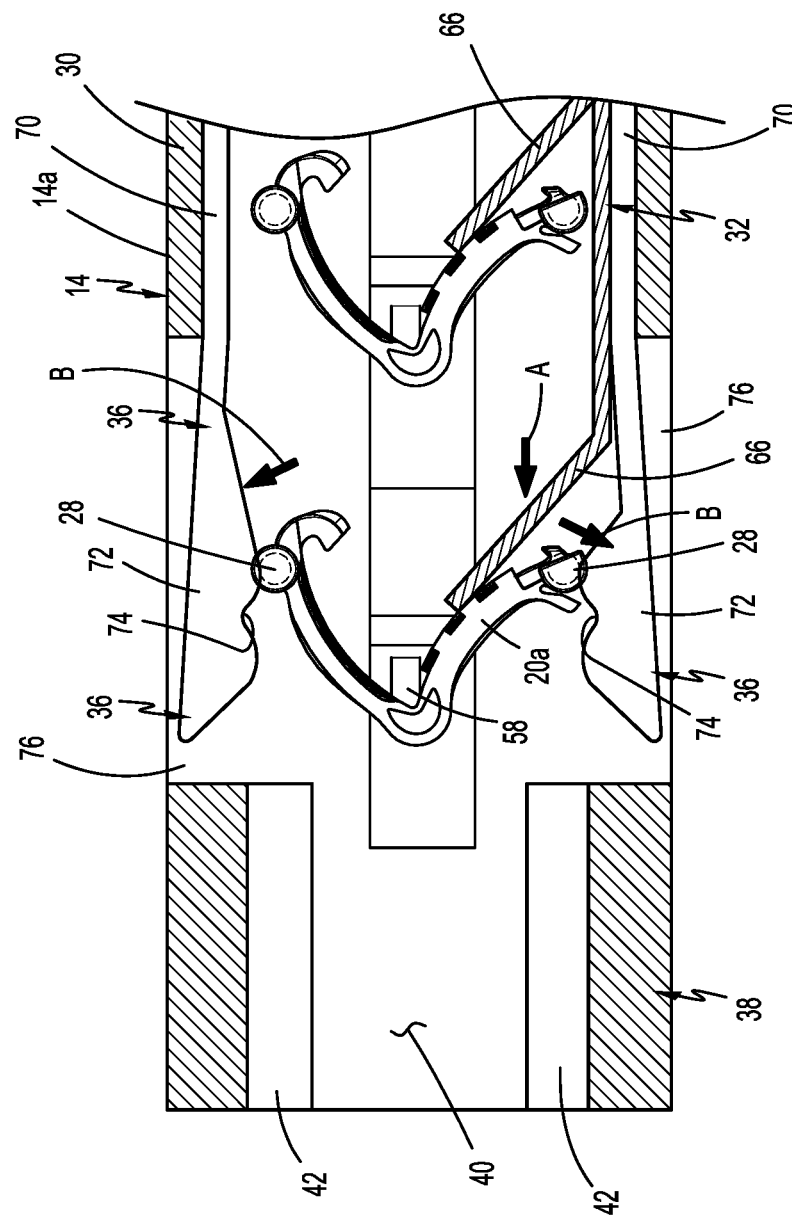
FIG. 6 is a cross-sectional view of the distal portion of the intraoperative ligation clip loading device shown in FIG. 1 as the plurality of ligation clips are advanced within the body of the intraoperative ligation clip loading device.

FIG. 6 illustrates the distal portion 14a of the elongate body 14 as the clip advancing member 32 is moved towards its advanced position to advance the plurality of clips 20 within the outer tube 30 of the elongate body 14. When the clip advancing member 32 is moved towards its advanced position in the direction indicated by arrow "A" in FIG. 6, each of the resilient fingers 66 of the clip advancing member 32 engages a respective ligation clip 20 and advances a respective ligation clip 20 from a clip retention pocket 56 to the next distally located clip retention pocket 56 defined between two opposed clip retainers 34. The distal-most clip 20a of the plurality of ligation clips 20 is advanced to a position between the clip locking arms 36. As the distal-most clip 20a is moved between the clip locking arms 36, the bosses 28 on the distal-most clip 20a engage the clip locking arms 36 to deflect the distal portions 72 of the clip locking arms 36 in the direction of arrow "B" into the cutouts 76 formed in the outer tube 30. As the distal-most ligation clip 20a moves to a position in which the bosses 28 of the ligation clip 20a are aligned with the concavities 74 in the clip locking arms 36, the clip locking arms 36 snap inwardly to position the bosses 28 within the concavities 74 to grip the ligation clip 20a between the clip locking arms 36.

As the clip advancing member 32 moves towards it advanced position, and the ligation clips 20 are received in the next distal clip retention pocket 56, the ligation clips 20 pass over one of the flexible tabs 58 of the clip retainers 34. As the ligation clips 20 pass over the flexible tabs 58, the flexible tabs 58 are deformed inwardly until the hinge portion 26 of the ligation clips 20 pass distally over the flexible tabs 58. Once the ligation clips 20 pass over the flexible tabs 58, the flexible tabs 58 return to a positon in which the stop surfaces 60 of the tabs 58 are aligned with the hinge portions 26 of the ligation clips 20 to prevent proximal movement of the ligation clips 20 within the outer tube 30.

Figure 7:
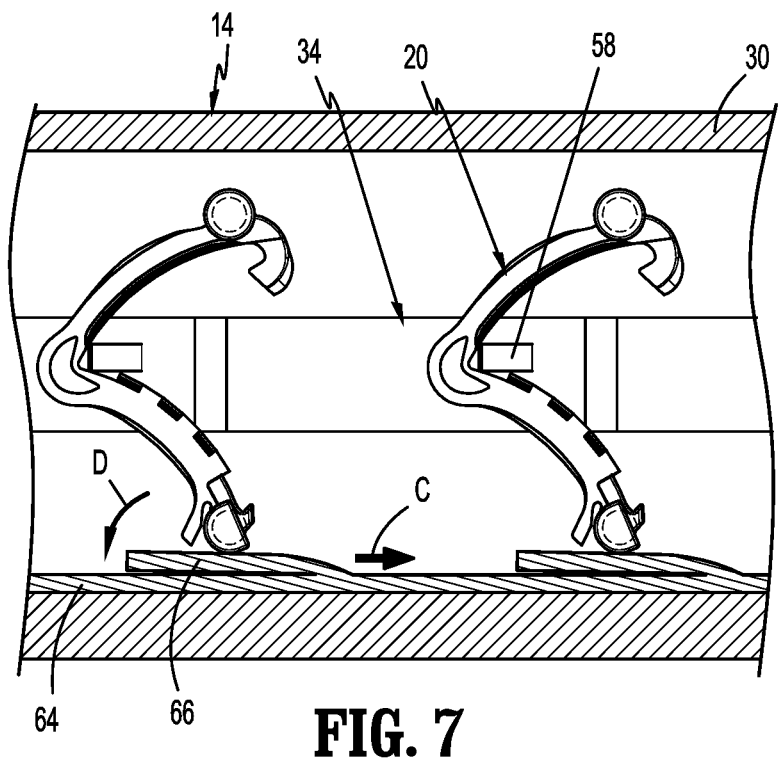
FIG. 7 is a cross-sectional, cutaway view of the central portion of the body of the intraoperative ligation clip loading device shown in FIG. 1 as the plurality of ligation clips are advanced within the body of the intraoperative ligation clip loading device.

FIG. 7 illustrates the clip advancing member 32 as the clip advancing member 32 moves in the direction of arrow "C" from its advanced position back towards its retracted position. As the clip advancing member 32 returns to its retracted position, the resilient fingers 66, which are angled towards the distal end of the outer tube 30, engage the ligation clips 30 positioned proximally of the respective resilient fingers 66. As described above, the ligation clips 20 are prevented from moving proximally within the outer tube 30 by the flexible tabs 58. As such, the resilient fingers 66 of the clip advancing members are deformed inwardly towards the elongate member 64 in the direction indicated by arrows "D" and pass beneath the respective ligation clips 20. In the retracted position of the clip advancing member 32, the resilient fingers 66 return to their undeformed positions shown in FIG. 3 located proximally of the respective ligation clips 20.

FIGS. 8-11 illustrate the loading device 10 as a ligation clip applier 100 is inserted into the distal portion 14a of the elongate body 14 to remove the distal-most ligation clip 20a (FIG. 10) from the loading device 10. The clip applier 100 includes an end effector 114 that includes jaws 112. The jaws 112 are movable in relation to each other to move a ligation clip 20 from an open position to a clamped position as known in the art. Each of the jaws 112 of the end effector 114 includes a distal portion including a hook portion 118 that defines a recess 120 that receives the bosses 28 of a ligation clip 20 to secure the ligation clip 20 to the clip applier 100.

In order to load a ligation clip 20 onto the clip applier 100, the jaws 112 of the clip applier 100 are inserted into the channels 42 of the guide member 38 in the distal portion 14a of the loading device 100. The channels 42 are aligned with the clip retention pockets 56 defined by the clip retainers 34 and with the clip locking arms 36 such that the jaws 112 of the clip applier 100 are aligned with the first and second beams 22 and 24 of the distal-most ligation clip 20a. When the jaws 112 engage the distal portion 72 of the clip locking arms 36, the clip locking arms 36 are deflected outwardly in the direction of arrows "E" in FIG. 10 to release the distal-most ligation clip 20a from the concavities 74 of the clip locking arms 36. As the jaws 112 of the clip applier 100 move further distally into the outer tube 30 of the loading device 10, the jaws 112 engage the beams 22 and 24 of the ligation clip 20a such that the bosses 28 are received in the recesses 120 of the hook portions 118 of the jaws 112. The stop surface 60 of the tab 58 of the clip retainers 34 engage the ligation clip 20a to prevent proximal movement of the ligation clip 20a within the outer tube 30. Once the bosses 28 are received within the recesses 120 of the jaw members 112, the end effector 114 of the clip applier 100 can be removed from the loading device 10 (FIG. 11) with the ligation clip 20 supported on the jaws 112. After the distal-most ligation clip 20a is removed from the elongate body 14 of the loading device 10, the actuator 18 of the handle assembly 12 of the loading device 10 can be actuated to advance the ligation clips 20 within the elongate body 14 to position the distal-most clip 20*a* in position between the clip locking arms 36 of the loading device 10.

The disclosed loading device 10 can be inserted through a cannula (not shown) to a surgical site within a body cavity to facilitate reloading of a single-use clip applier 100 during a surgical procedure at the surgical site. The elongate body 14 has a length to access the surgical site and to house a plurality of ligation clips 20, e.g., 5 or more ligation clips 20. The loading device 10 obviates any need to remove a single-use clip applier from a body cavity through a cannula to facilitate reloading of the clip applier 100.

Figure 14:
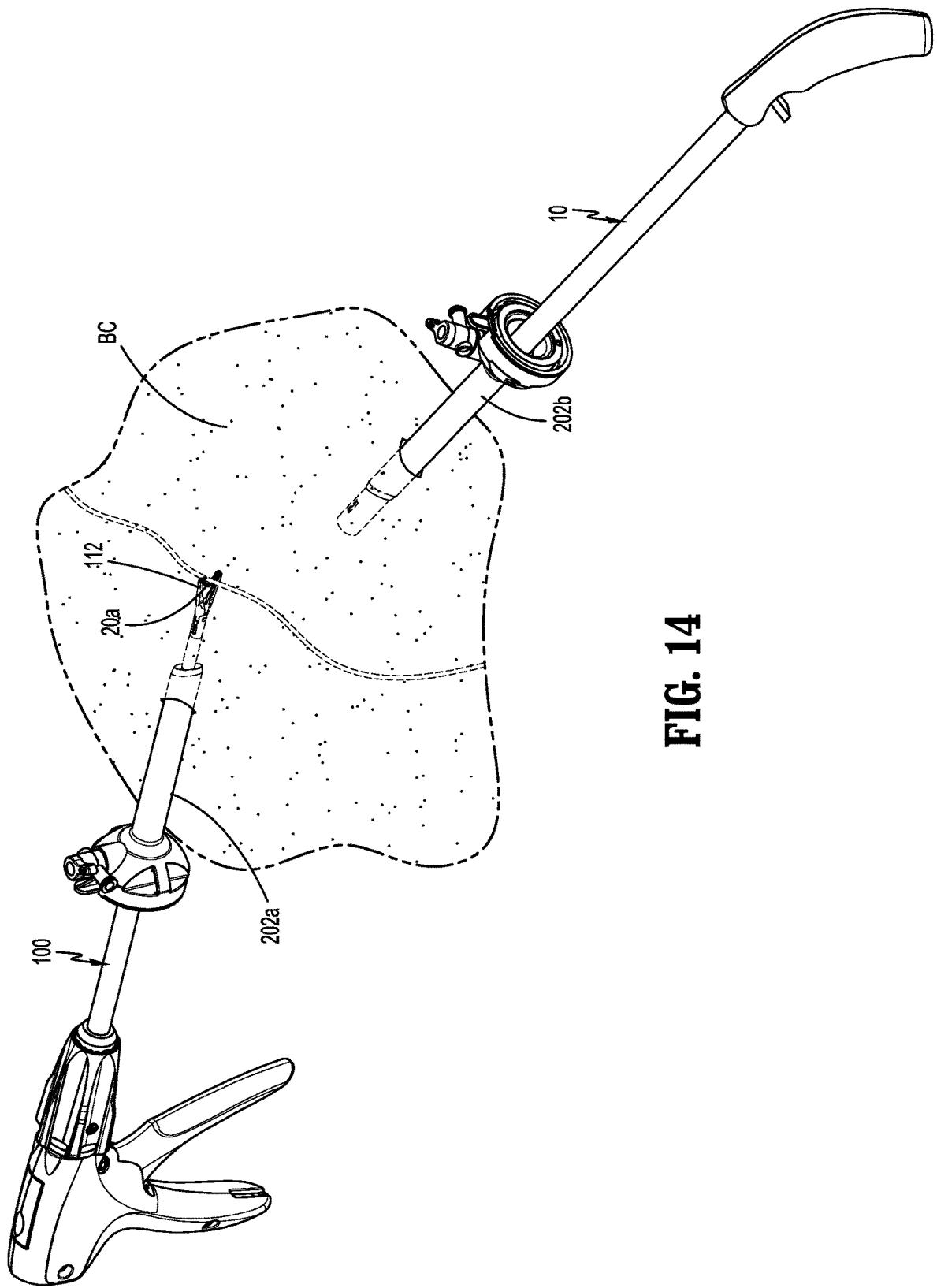
FIG. 14 is a perspective view of a body cavity of the patient shown in FIG. 13 with the intraoperative device shown in FIG. 1 and the clip applier shown in FIG. 11 positioned within the patient as a clip is applied to tissue.
Figure 15:
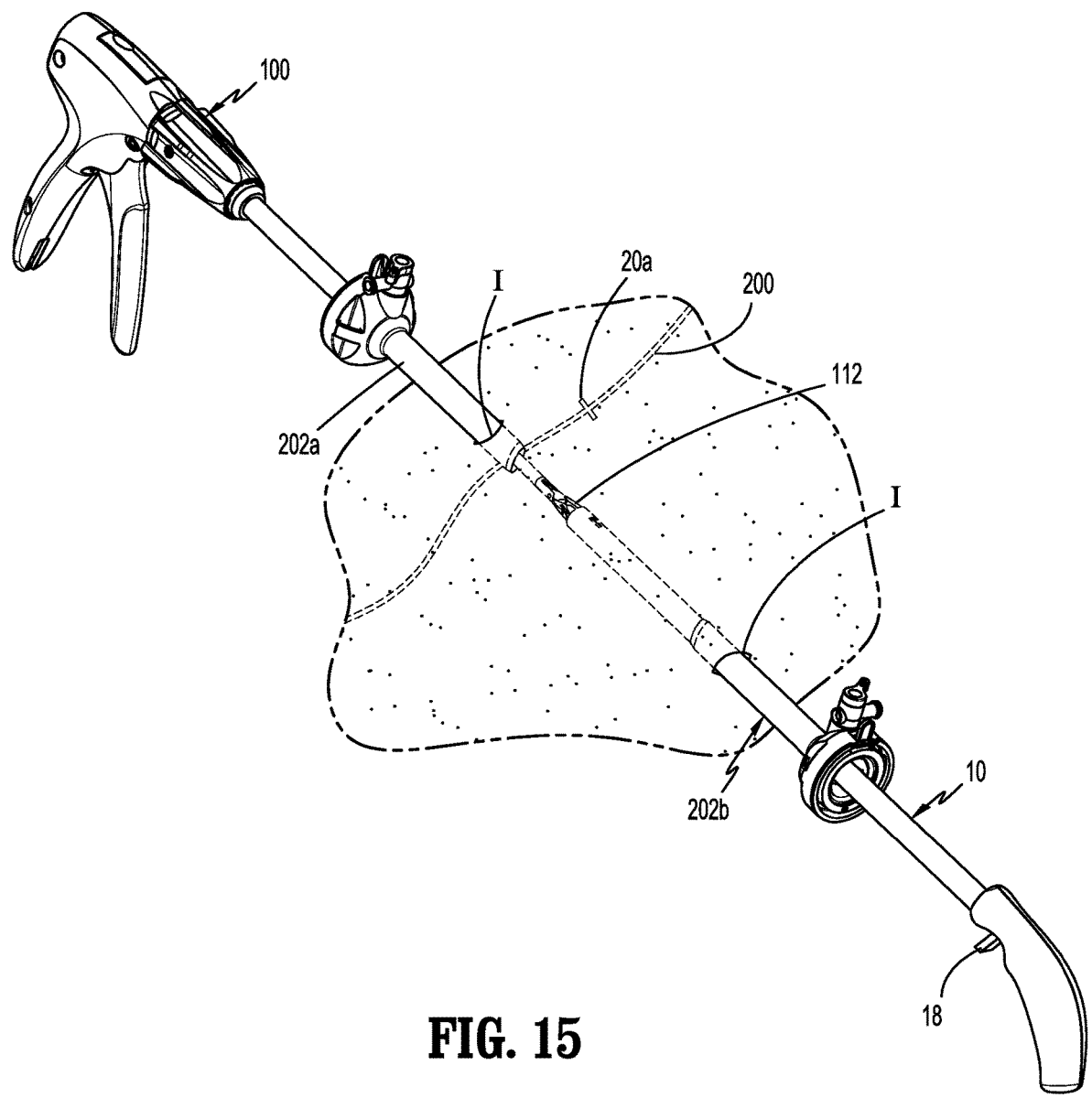
FIG. 15 is a perspective view of the body cavity of the patient shown in FIG. 14 with the intraoperative device shown in FIG. 1 and the clip applier shown in FIG. 11 positioned within the patient as a second clip is loaded into the clip applier.
Figure 16:
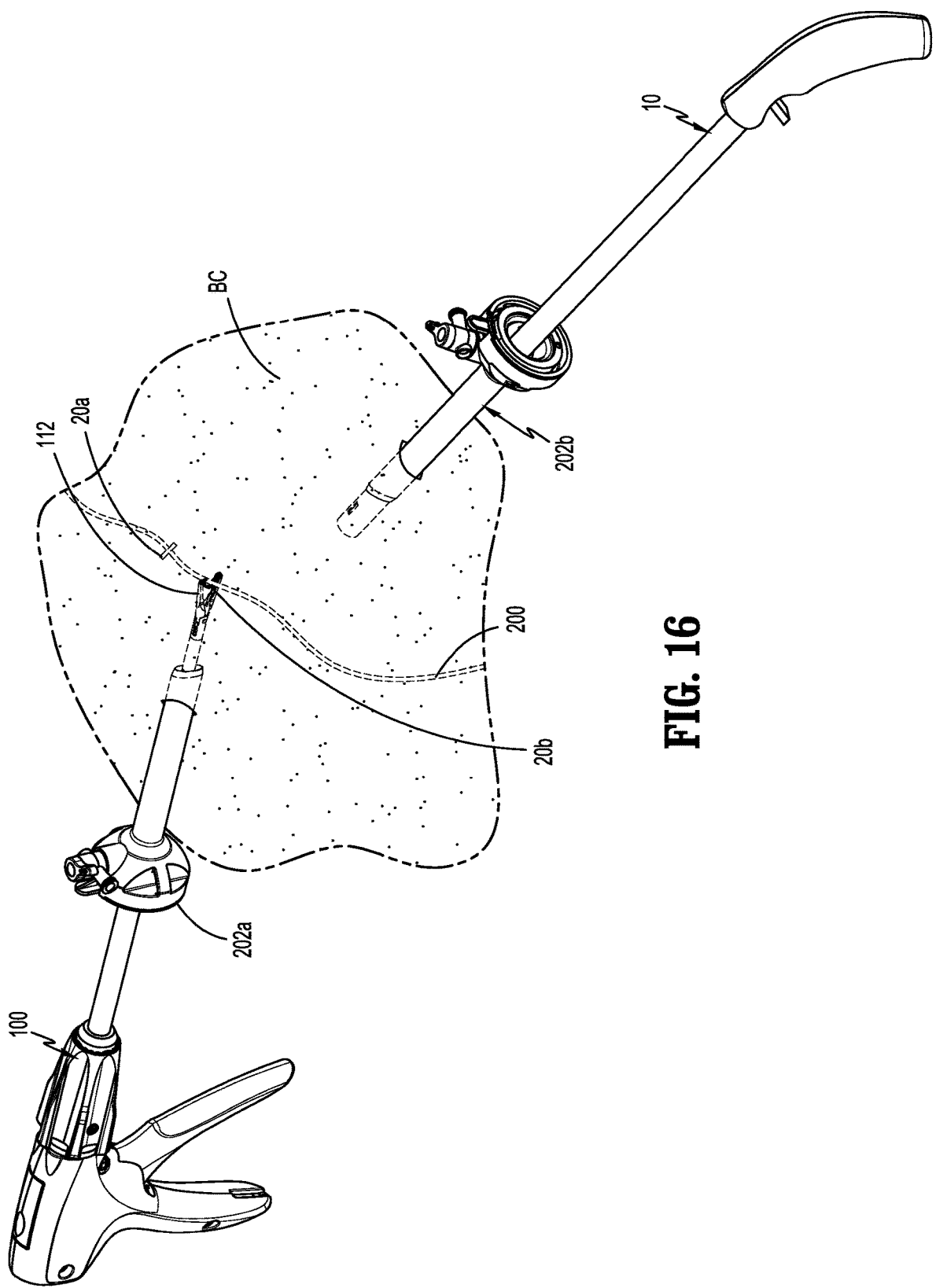
FIG. 16 is a perspective view of a body cavity of the patient shown in FIG. 13 with the intraoperative device shown in FIG. 1 and the clip applier shown in FIG. 11 positioned within a patient as the second clip is applied to tissue.

FIGS. 12-16 illustrate use of the loading device 10 and the clip applier 100 during a surgical procedure that requires more than one ligation clip 20 to ligate a body vessel 200. During the surgical procedure, the clip applier 100 and the loading device 10 are inserted through separate incisions "I" into a patient "P" to access a body cavity "BC" (FIG. 14). (Steps 300 and 302 in FIG. 12.) It is envisioned that cannulas 202*a* and 202*b* can be positioned within the incisions "I" and the clip applier 100 and the loading device 10 can be inserted through the cannulas 202*a* and 202*b*. In aspects of the disclosure, the clip applier 100 is loaded with a first clip 20*a* (FIG. 14) when the clip applier 100 is inserted through the cannula 202*a*. After the clip applier 100 is inserted through the cannula 202*a*, the clip applier 100 is manipulated to position the jaws 112 of the clip applier 100 about the body vessel 200 (FIG. 14) and the clip applier 100 is actuated to close the ligation clip 20*a* about the body vessel 200. (Step 304 in FIG. 12.) After the ligation clip 20*a* is closed about the body vessel 200, the jaws 112 of the clip applier 100 are removed from about the closed ligation clip 20*a* and are inserted into the distal end of the loading device 10 (FIG. 15) in the manner described above to retrieve a second ligation clip 20*b* (FIG. 16) from the loading device 10. (Step 306 in FIG. 12.) Once the second ligation clip 20*b* is supported between the jaws 112 of the clip applier 100, the jaws 112 of the clip applier 100 are withdrawn from the loading device 10 and the clip applier 100 is manipulated to reposition the jaws 112 of the clip applier 100 about the body vessel 200 (FIG. 16) (or about a different body vessel). (Step 308 in FIG. 12.) The clip applier 100 can now be actuated to close the second ligation clip 20*b* about the body vessel 200. This process can be repeated to reload the clip applier 100 after placement of each ligation clip 20. (Step 310 in FIG. 12.) In order to advance the clips 20*a-b* within the loading device 10 to allow the clips 20 within the loading device 10 to be retrieved by the clip applier 100, the actuator 18 of the loading device 10 must be operated to advance the clips 20*a-b* within the loading device 10.

It is envisioned that the clip applier 10 can be inserted through the cannula 202*a* without a ligation clip 20 supported between the jaws 112 of the clip applier 10. In such a case, the jaws 112 of the clip applier 100 can be inserted into the loading device 10 to retrieve a clip 20*a-b* prior to placement of the first ligation clip 20*a* about the body vessel 200. Inserting the clip applier 100 through the cannula 202*a* without a clip 20*a-b* loaded between the jaws 112 may allow the clip applier 100 to be inserted through a smaller diameter cannula.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. An intraoperative clip loading device comprising:
a handle assembly including a handle grip;
an elongate body having a proximal portion and a distal portion and defining a longitudinal axis, the proximal portion coupled to the handle assembly, the elongate body including an outer tube having a distal portion defining an opening and including an inner wall;
a guide member positioned on the distal portion of the outer tube, the guide member including diametrically opposed channels configured to receive jaws of a clip applier;
clip retainers supported on the inner wall of the outer tube, the clip retainers defining clip retention pockets along the longitudinal axis of the elongate body;
a plurality of ligation clips, each of the plurality of ligation clips being supported within one of the clip retention pockets and including a first beam, a second beam, and a hinge portion coupling the first beam to the second beam, each of the first and second beams including spaced bosses;
clip locking arms supported within the distal portion of the outer tube, the clip locking arms formed of a resilient material and being aligned with the opposed channels of the guide member, the clip locking arms each including a concavity configured to receive the spaced bosses of a respective one of the first and second beams of the ligation clips; and
a clip advancing member including an elongate member and a plurality of resilient fingers, each resilient finger of the plurality of resilient fingers engaging a respective one of the plurality of ligation clips, the clip advancing member movable within the outer tube from a retracted position to an advanced position to move the plurality of ligation clips distally within the outer tube.

2. The intraoperative clip loading device of claim 1, wherein the handle assembly includes an actuator, the actuator movable to move the clip advancing member between its retracted and advanced positions.

3. The intraoperative clip loading device of claim 1, wherein the clip retainers are formed of a resilient material, each of the clip retainers including a base portion secured to the inner wall of the outer tube and a longitudinal portion, the clip retainers positioned along opposite sides of the outer tube, each of the clip retainers aligned with another of the clip retainers such that two diametrically opposed clip retainers cooperate to define one of the clip retention pockets.

4. The intraoperative clip loading device of claim 3, wherein each of the clip retainers includes a transverse portion that interconnects the base portion and the longitudinal portion.

5. The intraoperative clip loading device of claim 4, wherein each of the longitudinal portions includes a flexible tab that is positioned to engage the hinge portion of a respective one of the plurality of ligation clips to prevent proximal movement of the respective ligation clip within the outer tube.

6. The intraoperative clip loading device of claim 5, wherein each of the flexible tabs is secured to the longitudinal portion of a respective one of the clip retainers in cantilevered fashion and includes a distal stop surface.

7. The intraoperative clip loading device of claim 1, wherein the clip locking arms are secured to the inner wall of the outer tube in cantilevered fashion, each of the clip locking arms including a proximal portion and a distal portion, the concavities being formed in the distal portions of the clip locking arms.

8. The intraoperative clip loading device of claim 7, wherein the outer tube defines cutouts that are aligned with the distal portions of the clip locking arms, the distal portions of the clip locking arms being deflectable outwardly into the cutouts to receive one of the plurality of ligation clips.

9. The intraoperative clip loading device of claim 1, wherein the resilient fingers of the clip advancing member extend inwardly in a distal direction from the elongate member of the clip advancing member into engagement with one of the first and second beams of a respective one of the plurality of ligation clips.

10. An intraoperative clip loading device comprising:
an elongate body having a proximal portion and a distal portion and defining a longitudinal axis, the elongate body including an outer tube having a distal portion defining an opening and including an inner wall;
clip retainers supported on the inner wall of the outer tube, each of the clip retainers having a base portion secured to the inner wall and a longitudinal portion, the clip retainers positioned along opposite sides of the outer tube such that each pair of two diametrically opposed clip retainers cooperate to define one of a plurality of clip retention pockets between their longitudinal portions, each of the longitudinal portions including a flexible tab having a stop surface;
a plurality of ligation clips, each of the plurality of ligation clips being supported within one of the clip retention pockets and including a first beam, a second beam, and a hinge portion coupling the first beam to the second beam, each of the first and second beams including spaced bosses, wherein the stop surfaces of the flexible tabs of the clip retainers are positioned to engage the hinge portions of the plurality of ligation clips to prevent proximal movement of the plurality of ligation clips within the outer tube;
clip locking arms supported within the distal portion of the outer tube, the clip locking arms being formed of a resilient material and being aligned with opposed channels of a guide member, the clip locking arms each including a concavity configured to receive the spaced bosses of a respective one of the first and second beams of the ligation clips; and
a clip advancing member including an elongate member and a plurality of resilient fingers, each resilient finger of the plurality of resilient fingers engaging a respective one of the plurality of ligation clips, the clip advancing member movable within the outer tube from a retracted position to an advanced position to move the plurality of ligation clips distally within the outer tube.

11. The intraoperative clip loading device of claim 10, further including a handle assembly including a handle grip and an actuator, the actuator being coupled to the clip advancing member such that movement of the actuator moves the clip advancing member between its retracted and advanced positions.

12. The intraoperative clip loading device of claim 10, wherein the guide member is positioned on the distal portion of the outer tube, and the opposed channels are configured to receive jaws of a clip applier.

13. The intraoperative clip loading device of claim 10, wherein the clip retainers are formed of a resilient material.

14. The intraoperative clip loading device of claim 13, wherein each clip retainer includes a transverse portion that interconnects the base portion of the clip retainer and the longitudinal portion of the clip retainer.

15. The intraoperative clip loading device of claim 10, wherein each of the flexible tabs is secured to the longitudinal portion of a respective one of the clip retainers in cantilevered fashion.

16. The intraoperative clip loading device of claim 10, wherein the clip locking arms are secured to the inner wall of the outer tube in cantilevered fashion, each of the clip locking arms including a proximal portion and a distal portion, the concavities being formed in the distal portions of the clip locking arms.

17. The intraoperative clip loading device of claim 16, wherein the outer tube defines cutouts that are aligned with the distal portions of the clip locking arms, the distal portions of the clip locking arms being deflectable outwardly into the cutouts to receive one of the plurality of ligation clips.

18. The intraoperative clip loading device of claim 10, wherein the resilient fingers of the clip advancing member extend inwardly in a distal direction from the elongate member of the clip advancing member into engagement with one of the first and second beams of a respective one of the plurality of ligation clips.

19. An intraoperative clip loading device comprising:
a handle assembly including a handle grip and an actuator;
an elongate body having a proximal portion and a distal portion and defining a longitudinal axis, the proximal portion coupled to the handle assembly, the elongate body including an outer tube having a distal portion defining an opening and an inner wall;
clip retainers supported on the inner wall of the outer tube, the clip retainers defining clip retention pockets along the longitudinal axis of the elongate body, the clip retainers formed of a resilient material, each of the clip retainers including a base portion secured to the inner wall of the outer tube and a longitudinal portion, the clip retainers positioned along opposite sides of the outer tube, each of the clip retainers aligned with another of the clip retainers such that two diametrically opposed clip retainers cooperate to define one of the clip retention pockets;
a plurality of ligation clips, each of the plurality of ligation clips being supported within one of the clip retention pockets and including a first beam, a second beam, and a hinge portion coupling the first beam to the second beam, each of the first and second beams including spaced bosses;
clip locking arms supported within the distal portion of the outer tube, the clip locking arms formed of a resilient material and being aligned with opposed channels in a guide member, the clip locking arms each including a concavity configured to receive the spaced bosses of a respective one of the first and second beams of the ligation clips; and
a clip advancing member including an elongate member and a plurality of resilient fingers, each resilient finger of the plurality of resilient fingers engaging a respective one of the plurality of ligation clips, the clip advancing member movable within the outer tube from a retracted position to an advanced position in response to actuation of the actuator to move the plurality of ligation clips distally within the outer tube.

20. The intraoperative clip loading device of claim 19, wherein each of the clip retainers includes a transverse portion that interconnects the base portion and the longitudinal portion.

\* \* \* \* \*